(12) United States Patent
Ballabio et al.

US009127074B2

(10) Patent No.: US 9,127,074 B2
(45) Date of Patent: Sep. 8, 2015

(54) TFEB VARIANTS AND USES THEREOF

(75) Inventors: Andrea Ballabio, Naples (IT); Carmine Settembre, Naples (IT); Diego Luis Medina Sanabria, Naples (IT)

(73) Assignee: FONDAZIONE TELETHON, Rome (IT)

( * ) Notice: Subject to any disclaimer, the term of this patent is extended or adjusted under 35 U.S.C. 154(b) by 0 days.

(21) Appl. No.: 14/003,505

(22) PCT Filed: Mar. 7, 2012

(86) PCT No.: PCT/EP2012/053921
§ 371 (c)(1),
(2), (4) Date: Oct. 3, 2013

(87) PCT Pub. No.: WO2012/120044
PCT Pub. Date: Sep. 13, 2012

(65) Prior Publication Data
US 2014/0038897 A1 Feb. 6, 2014

Related U.S. Application Data

(60) Provisional application No. 61/449,751, filed on Mar. 7, 2011, provisional application No. 61/579,793, filed on Dec. 23, 2011, provisional application No. 61/596,485, filed on Feb. 8, 2012.

(51) Int. Cl.
| | |
|---|---|
| *C07K 14/435* | (2006.01) |
| *A61K 38/17* | (2006.01) |
| *A61K 31/00* | (2006.01) |
| *C07K 14/47* | (2006.01) |
| *A61K 31/436* | (2006.01) |
| *A61K 31/437* | (2006.01) |
| *A61K 31/4375* | (2006.01) |
| *A61K 31/4523* | (2006.01) |
| *A61K 31/454* | (2006.01) |
| *A61K 31/4709* | (2006.01) |
| *A61K 31/496* | (2006.01) |
| *A61K 31/498* | (2006.01) |
| *A61K 31/5377* | (2006.01) |
| *A61K 31/5386* | (2006.01) |
| *A61K 31/675* | (2006.01) |
| *A61K 38/06* | (2006.01) |
| *A61K 38/00* | (2006.01) |

(52) U.S. Cl.
CPC .............. *C07K 14/435* (2013.01); *A61K 31/00* (2013.01); *A61K 31/436* (2013.01); *A61K 31/437* (2013.01); *A61K 31/4375* (2013.01); *A61K 31/454* (2013.01); *A61K 31/4523* (2013.01); *A61K 31/4709* (2013.01); *A61K 31/496* (2013.01); *A61K 31/498* (2013.01); *A61K 31/5377* (2013.01); *A61K 31/5386* (2013.01); *A61K 31/675* (2013.01); *A61K 38/06* (2013.01); *C07K 14/4702* (2013.01); *A61K 38/00* (2013.01)

(58) Field of Classification Search
CPC .............................. C07K 14/435; A61K 38/17
See application file for complete search history.

(56) References Cited

FOREIGN PATENT DOCUMENTS

WO 2010/092112 A1 8/2010

OTHER PUBLICATIONS

Carr et al., A helix-loop-helix protein related to the immunoglobulin E box-binding proteins. Mol. Cell. Biol. 10, 4384-4388, 1990.*
Sardiello Marco, et al: "A gene network regulating lysosomal biogenesis and function", Science, American Association for the Advancement of Science, Washington, DC; US, vol. 325, No. 5939, Jul. 24, 2009, pp. 473-477, [Retrieved on Jun. 25, 2009]; abstract, Fig. 1-2 and p. 476.
Dehay Benjamin, et al: "Pathogenic Lysosomal Depletion in Parkinson's Disease", Journal of Neuroscience, New York, NY, US, vol. 30, No. 37, Sep. 15, 2010, pp. 12535-12544, abstract, p. 12540.

* cited by examiner

*Primary Examiner* — Ruixiang Li
(74) *Attorney, Agent, or Firm* — Lucas & Mercanti, LLP

(57) ABSTRACT

The invention refers to TFEB related molecules, as variants, mutants, truncated proteins, chimeras etc. that are constitutively localized in the nucleus of a eukaryote cell. Such molecules have a therapeutic applicability in all of disorders that need of an induction of the cell authophagic/lysosomal system, as lysosomal storage disorders, neurodegenerative diseases, hepatic diseases, muscle diseases and metabolic diseases.

5 Claims, 21 Drawing Sheets

S142

| | | | |
|---|---|---|---|
| sp | P19484 | TFEB_HUMAN | LSSSAGNSAP NSPMAMLHIG |
| tr | B0KWN0 | TFEB_CALJA | LSSSAGNSAP NSPMAMLHIG |
| tr | A8MN25 | TFEB_PAPAN | LSSSAGNSAP NSPMAMLHIG |
| tr | B7NZJ9 | TFEB_RABIT | LSTSAGNSAP NSPMAMLHIS |
| tr | Q4KLM8 | TFEB_RAT | LSTSAGNSAP NSPMAMLHIS |
| sp | Q9R210 | TFEB_MOUSE | LSTSAGNSAP NSPMAMLHIS |
| tr | Q6P203 | TCFEB_MOUSE | LSTSAGNSAP NSPMAMLHIS |
| tr | C3PT72 | TFEB_DASNO | LSSSAGNSAP NSPMAMLHIG |
| tr | B5SNL7 | TFEB_OTOGA | LSSSAGNSAP NSPMAMLHIG |
| tr | B3RFC8 | TFEB_SORAR | LSSSASNSAP NSPMAMLHIG |
| tr | Q08D59 | TFEB_XENTR | LSSSAGNSAP NSPMARMNLC |
| tr | A4IID0 | MITF_XENTR | MPPGPGSSAP NSPMALLTIG |
| tr | Q76DN4 | MITFA_XENLA | MPPGPGSSAP NSPMALLTIG |
| tr | O73871 | MITF_CHICK | MPPGTGSSAP NSPMALLTLN |
| tr | Q76DN2 | MITFA_XENLA | MPPGPGSSAP NSPMALLTIG |
| tr | D2JUK2 | MITF_PIG | MPPVPGSSAP NSPMAMLTLN |
| sp | O75030 | MITF_HUMAN | MPPVPGSSAP NSPMAMLTLN |
| sp | Q08874 | MITF_MOUSE | MPPVPGSSAP NSPMAMLTLN |
| sp | Q64092 | TFE3_MOUSE | HATGPTGSAP NSPMALLTIG |
| tr | A2AEW1 | TCFE3_MOUSE | HATGPTGSAP NSPMALLTIG |
| sp | P19532 | TFE3_HUMAN | HTTGPTGSAP NSPMALLTIG |
| sp | Q05B92 | TFE3_BOVIN | HAPGPTSSAP NSPMALLTIG |
| tr | Q561Z2 | TFE3A_DANRE | ELAPAASSTP SSPLAVLSLG |
| tr | Q7SZX8 | TFE3B_DANRE | EMGPSASSAP NSPMAHLNLG |
| tr | A9UJQ4 | MITFA_9CICH | MPPGPGSSAP NSPMALLTLS |
| tr | Q6TGR1 | MITF_BOVIN | MPPVPGSSAP NSPMAMLTLN |
| tr | B6E281 | MITF_CHICK | MPPGTGSSAP NSPMAMLTLN |
| tr | Q5XHC0 | TFE3_XENLA | AIOPSASSAP NSPLAMLKID |
| tr | Q864F3 | MITF_CANFA | MPPVPGSSAP NSPMAMLTLN |
| tr | Q90XP4 | MITFB_DANRE | MPPGPGNSAP NSPMALLTLN |
| tr | Q9PWC2 | MITFA_DANRE | MTPGPGASAP NSPMALLTLN |
| tr | B5UB80 | MITFA_PAROL | MPPGPGSSAP NSPMALLTLS |
| tr | Q76DN5 | MITFM_XENLA | MPPGPGSSAP NSPMALLTIG |

Fig. 14

TFEB VARIANTS AND USES THEREOF

CROSS-REFERENCE TO RELATED APPLICATIONS

This application is a 371 of PCT/EP2012/053921, filed Mar. 7, 2012, which claims the benefit of U.S. Provisional Application Nos. 61/449,751, filed Mar. 7, 2011, 61/579,793, filed Dec. 23, 2011, and 61/596,485, filed Feb. 8, 2012, the contents of each of which are incorporated herein by reference.

FIELD OF THE INVENTION

The invention refers to TFEB related molecules, as variants, mutants, truncated proteins, chimeras etc. that are constitutively localized in the nucleus of a eukaryote cell. Such molecules have a therapeutic applicability in all of disorders that need of an induction of the cell authophagic/lysosomal system, as lysosomal storage disorders, neurodegenerative diseases, hepatic diseases, muscle diseases and metabolic diseases.

BACKGROUND OF THE INVENTION

Autophagy is a catabolic process that relies on the cooperation of two distinct types of cellular organelles, autophagosomes and lysosomes (1). During starvation the cell expands both compartments to enhance degradation and recycling processes.

The lysosome maintains cellular homeostasis and mediates a variety of physiological processes, including cellular clearance, lipid homeostasis, energy metabolism, plasma membrane repair, bone remodeling, and pathogen defense. All these processes require an adaptive and dynamic response of the lysosome to environmental cues. Indeed, physiologic cues, such as aging and diet, and pathologic conditions, which include lysosomal storage diseases (LSDs), neurodegenerative diseases, injuries and infections may generate an adaptive response of the lysosome (34, 35, 36).

The understanding of the mechanisms that regulate lysosomal function and underlying lysosomal adaptation is still in an initial phase. A major player in the regulation of lysosomal biogenesis is the basic Helix-Loop-Helix (bHLH) leucine zipper transcription factor, TFEB (2). Among the identified TFEB transcriptional targets are lysosomal hydrolases, which are involved in substrate degradation, lysosomal membrane proteins that mediate the interaction of the lysosome with other cellular structures, and components of the vacuolar H+-ATPase (vATPase) complex, which participate to lysosomal acidification (37, 2).

WO2010/092112 refers to molecules able to enhance the cellular degradative pathway acting on the so called CLEAR element; among them TFEB is listed.

SUMMARY OF THE INVENTION

The applicants showed that during starvation the cell activates a transcriptional program that controls major steps of the autophagic pathway, including autophagosome formation, autophagosome-lysosome fusion and substrate degradation. The transcription factor EB (TFEB), a previously identified master gene for lysosomal biogenesis (2), coordinates this program by driving expression of both autophagy and lysosomal genes.

The applicants found that nuclear localization and activity of TFEB are regulated by specific serine phosphorylations. Similar to starvation, pharmacological or gene mutation based inhibition of specific phosphorylation induces autophagy by activating TFEB. These data unveil a novel, kinase-dependent, mechanism involved in the regulation of the lysosomal-autophagic pathway by controlling the biogenesis and partnership of two cooperating cellular organelles.

Therefore it is an object of the invention herein disclosed a TFEB variant protein that is constitutively localized in the nucleus of a eukaryote cell. The TFEB variant protein of the invention comprises a substitution or alteration of a serine residue to render the same phosphorylation insensitive. The ordinary skilled in the art would recognize that other amino acid substitutions, other than tyrosine, can be made to render the TFEB variant phosphorylation insensitive. For example the serine residue can be replaced with a natural amino acid, for example a neutral amino acid as alanine, or unnatural amino acid. A TFEB variant protein that is constitutively localized in the nucleus of a eukaryote cell comprises mutants, truncated proteins, chimeras of TFEB.

In a preferred embodiment the TFEB variant protein consists of an amino acid sequence comprised in Seq. Id No. 2 and wherein the substitution of a serine residue is at SER 142 and/or at SER 211 of Seq. Id No. 2. Preferably the amino acid sequence comprised in Seq. Id No. 2 is from aa. 117 to aa. 166 and the substitution of a serine residue is at SER 142 of Seq. Id No. 2 (Seq Id No. 4). Alternatively the amino acid sequence essentially consists of Seq. Id No. 2 and the substitution of a serine residue is at SER 142 and/or at SER 211. In a most preferred embodiment the substitution(s) at SER 142 and/or SER 211 of Seq. Id. No. 2 are to ALA.

It is another object of the invention the TFEB variant protein as above disclosed for medical use.

The TFEB variant protein as above disclosed is advantageously used in the treatment of a disorder that needs of the induction of the cell authophagic/lysosomal system, preferably for use in the treatment of any of the following pathologies: lysosomal storage disorders, neurodegenerative diseases, hepatic diseases, muscle diseases and metabolic diseases.

Examples of lysosomal storage disorder are: activator deficiency/GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, Gaucher disease (including Type I, Type II, and Type III), GM1 gangliosidosis (including infantile, late infantile/juvenile, adult/chronic), I-cell disease/mucolipidosis II, infantile free sialic acid storage disease/ISSD, juvenile hexosaminidase A deficiency, Krabbe disease (including infantile onset, late onset), metachromatic leukodystrophy, pseudo-Hurler polydystrohpy/mucolipidosis IIIA, MPS I Hurler syndrome, MPS I Scheie syndrome, MPS I Hurler-Scheie syndrome, MPS II Hunter syndrome, Sanfilippo syndrome type AMPS IIIA, Sanfilippo syndrome type B/MPS IIIB, Morquio type AMPS IVA, Morquio Type B/MPS IVB, MPS IX hyaluronidase deficiency, Niemann-Pick disease (including Type A, Type B, and Type C), neuronal ceroidlipofuscinoses (including CLN6 disease, atypical late infantile, late onset variant, early juvenile Baten-Spielmeyer-Vogt/juvenile NCL/CLN3 disease, Finnish variant late infantile CLN5, Jansky-Bielschowsky disease/late infantile CLN2/TPP1 disease, Kufs/adult-onset NCL/CLN4 disease, northern epilepsy/variant late infantile CLN8, and Santavuori-Haltia/infantile CLN1/PPT disease), beta-mannosidosis, Pompe disease/glycogen storage disease type II, pycnodysostosis, Sandhoff disease/adult onset/GM2 gangliosidosis, Sandhoff disease/GM2 gangliosidosis infantile, Sandhoff disease/GM2 gangliosidosis juvenile, Schindler disease, Salla disease/sialic acid storage disease, Tay-Sachs/GM2 gangliosidosis, Wolman disease, Multiple Sulfatase Deficiency.

Examples of hepatic diseases are: Alpha1 antitrypsin deficiency and Fatty liver disease.

Examples of muscle diseases are: Autophagic Vacuolar Myopathies and X-linked myopathy with excessive autophagy.

Examples of metabolic diseases are: hypercholesterolemy and fatty liver disease.

Examples of neurodegenerative diseases are: Alzheimer's disease, Parkinson's disease, Huntington's disease, Creutzfeldt-Jakob disease, and spinocerebellar ataxia.

It is a further object of the invention a nucleic acid comprising a coding sequence encoding for the TFEB variant protein as above disclosed. Preferably the nucleic acid comprises the sequence of Seq. Id No. 3.

It is a further object of the invention an expression vector comprising under appropriate regulative sequences the nucleic acid as above disclosed.

The expression vector of the invention may advantageously be used for gene therapy.

It is a further object of the invention a method for increasing the production of endogenous or recombinant lysosomal enzymes in an ex vivo cultured cell comprising the steps of:—introducing the nucleic acid according or the expression vector as above disclosed in said cell and—allowing the expression of the encoded TFEB variant protein.

It is a further object of the invention a method of treating a disorder by administering to a subject a therapeutically effective amount of the TFEB variant protein as above disclosed, preferably when the disorder is alleviated by the induction of the cell authophagic/lysosomal system.

More preferably the disorder is selected from the group comprising lysosomal storage disorders, neurodegenerative diseases, hepatic diseases, muscle diseases and metabolic diseases. Examples of such disorders were above provided.

BRIEF DESCRIPTION OF THE DRAWINGS

FIG. 14 Multiple sequence alignment of TFEB-human S142 phosphorylation site with TFEB paralogues, MITF and relevant TFEB-related family members. TFEB_human homologs were identified by BLAST (2.2.17) search against UniProtKB database at ExPASy Proteomics Server. The applicants removed the hits with "putative", "uncharacterized" and "cDNA" keywords and hits without gene names. Next, the applicantsauthors aligned the remaining homologs with ClustalW (1.82). The multiple sequence alignment was generated by Seaview. The figure shows only a 20 amino acid-long segment of TFEB HUMAN sequence aligned with other proteins from TFEB, MITF, TCFEB, TFE3 and TCFE3 families. "sp" stands for SwissProt entry, while "tr" denotes Tremble entry. P19484 is a UniProrKB accession code. TFEB HUMAN indicates gene name and species name respectively.

DETAILED DESCRIPTION OF THE INVENTION

Materials and Methods

Cell Culture and Media and Drugs and Cellular Treatment

Figure 2:
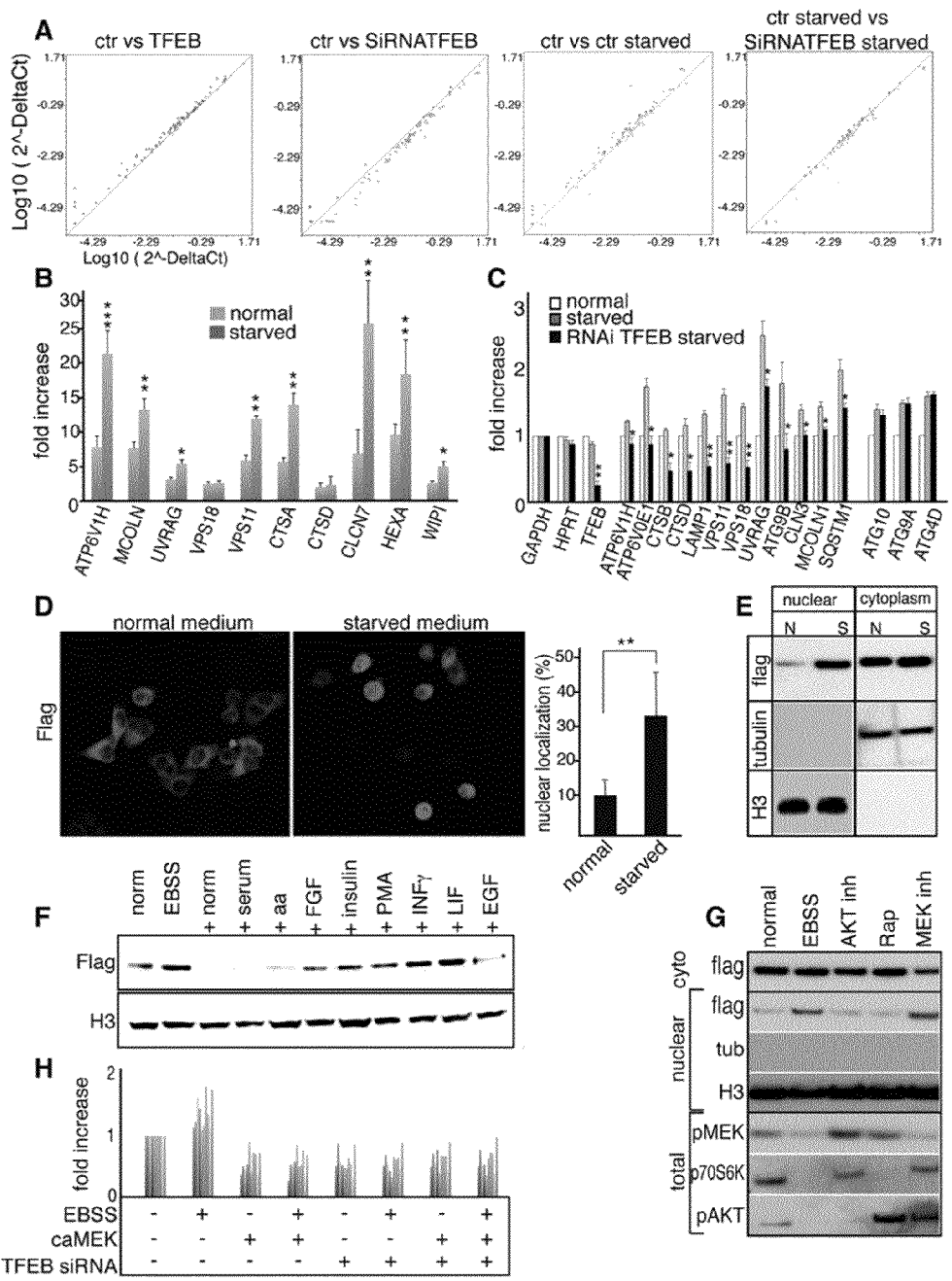
FIG. 2 Starvation regulates TFEB nuclear translocation and activity. (A) Scatter Plot graphs displaying the logarithmic value of the fold change differences in the relative expression levels of 51 autophagy-related genes in HeLa cells cultured in different conditions. X-axis=control group. Y-axis=treated group. Circles represent genes with increased (red) or decreased (green) fold change. Comparisons were as indicated. (B) Chromatin immunoprecipitation (ChIP) analysis. The histogram shows the amount of immunoprecipitated DNA as detected by qPCR assay. Values were normalized to the input and plotted as relative enrichment over a mock control. Experiments were performed in triplicate. (C) qPCR analysis of TFEB-target gene expression in normal, starved, and in TFEB-siRNA starved cells. GAPDH and HPRT represents housekeeping genes, while ATG10, ATG9A and ATG4D represent control genes (non-TFEB target genes). (D-F) HeLa cells stably overexpressing TFEB were left untreated or nutrient starved for 4 h. (D) Five fields containing 50-100 cells/each were analyzed for TFEB nuclear localization. P value (*)=<0.01. (E) Cells were subjected to nuclear/cytosolic fractionation and blotted with Flag antibody. H3 and tubulin were used as nuclear and cytosolic markers, respectively. (F) Nuclear fractions were blotted with Flag and H3 (loading control) antibodies. (G) Western blot analysis of Flag, tubulin and H3 in nuclear extracts prepared from normal, starved and starved/stimulated with normal media cells for 1 h (normal) or pretreated with AP-2 (AKT inhibitor), Rapamycin (mTOR inhibitor) and U0126(MEK inhibitor) 1 h prior to media stimulation. Total extracts were used to verify the efficiency of the inhibitors. (H) qPCR analysis of lysosomal and autophagic genes in TFEB siRNA or TFEB-scrambled control cells transfected with either a constitutive active MEK (caMEK) plasmid or with an empty vector. Starvation was performed where indicated. (All error bars represent standard deviations. T-test (unpaired) p value (*)<0.05, (**)<0.01)

HeLa and COS and HEK-293T cells were purchased from ATCC. Cells were cultured in the following media: (normal) DMEM high glucose supplemented with 10% FBS; (starvation) HBSS media with Ca and Mg supplemented with 10 mM HEPES; (Serum) EBSS supplemented with 20% FBS; (amino acid media) Glucose and serum free DMEM; Drugs treatment: Rapamycin (2.5 mg/ml, SIGMA) 2-4 h otherwise indicated; Bafilomycin, (400 nM, SIGMA) 2-4 h; Insulin (100 ng/ml SIGMA) for 2 h; EGF, FGF (BD biosciences); LIF (100 ng/ml; ESGRO, Millipore) 2 h; PMA (1 µs/ml) 2 h. U0126 (MEKi) were used at 25 mM (Cell Signaling), API2 (AKT inhibitor) were used at 1 mM. Lysosomal inhibitors were pepstatin and E64 (10 mg/ml 4 h SIGMA). The following drugs were used in the experiments of FIGS. 18-2: Rapamycin (2.5 µM, otherwise indicated) from SIGMA; Torin 1 (250 nM250 nM, otherwise indicated) from TOCRIS; U0126 (50 µM50 µM) from Cell Signaling technology; Chloroquine (100 µM100 µM) from SIGMA; Salicylihalamide A (2 µM2 µM) was a kind gift from Jeff De Brabander (UT Southwestern).

Primary hepatocytes were generated as follow: 2-month-old mice were deeply anaesthetized with Avertin (240 mg/kg) and perfused first with 25 ml of HBSS (Sigma H6648) supplemented with 10 mM HEPES and 0.5 mM EGTA and after with a similar solution containing 100 U/ml of Collagenase (Wako) and 0.05 mg/ml of Trypsin inhibitor (Sigma). Liver was dissociated in a petri dish, cell pellet was washed in HBSS and plated at density of $5 \times 10^5$ cells/35 mm dish and cultured in William's medium E supplemented with 10% FBS, 2 mM glutamine, 0.1 mM Insulin, 0.1 mM Dexamethasone and pen/strep. The next day, cells were treated as described in the text. Sin1−/− and control MEFs were generated as previously described (46) and maintained in DMEM supplemented with 10% FBS, glutamine and pen/strep.

Generation of a Tcfeb$^{flox}$ mouse line

The applicants used publicly available embryonic stem (ES) cell clones (http://www.eucomm.org/) in which Tcfeb was targeted by homologous recombination at exons 4 and 5. The recombinant ES cell clones were injected into blastocysts, which were used to generate a mouse line carrying the engineered allele. Liver-specific KO was generated crossing the Flox/Flox mice with a transgenic line expressing the CRE under the Albumin promoter (ALB-CRE) obtained from the Jackson laboratory. All procedures involving mice were approved by the Institutional Animal Care and Use Committee of the Baylor College of Medicine.

Transfection, Plasmids and siRNA

Both plasmids and siRNA were transfected with lipofectamine LTX (Invitrogen) using a reverse transfection protocols. siRNA-transfected cells were collected after 48 or 72 h. siRNA TFEB were used at 50 nM (Dharmacon), siRNA ERK1/2 were used at 100 nM (Cell Signaling).

Cells were transiently transfected with DNA plasmids pRK5-mycPAT1, pCEP4-TFEB-his, pC1G2-TFEB, and p3×FLAG-CMVTFEB using lipofectamine2000 or LTX (Invitrogen) according to the protocol from manufacturer. Site-direct mutagenesis was performed according to the manufacturer instructions (Stratagene) verifying the correct mutagenesis by sequencing.

Western Blotting

Cells or tissues were solubilized in RIPA buffer supplemented with protease (ROCHE) and Phosphatase (SIGMA) inhibitors. From 10 to 30 micrograms were loaded on 4-12% Bis-Tris gel (NUPAGE, Invitrogen), transferred to PVDF membranes and analyzed by western blot using the ECL method (Pierce). The following antibodies were used: LC3 (Novus Biological), FLAG, b-ACTIN, TUBULIN (SIGMA), HA (Covance), H3, ERK1/2, p-ERK1/2, p-AKT, p-70S6K (Cell Signaling), ERK2 (Santa Cruz). Protein levels were quantified by using ImageJ software analysis.

Nuclear/Cytosolic Fractionation

Cells were seeded at 50% of confluence in 6 well dishes and serum starved overnight (ON). Normal medium was added the following day either in presence of DMSO or kinase inhibitors. Subcellular fractionation was carried out as previously reported. Briefly, cells were lysed in 0.5 Triton X-100 lysis buffer (50 mM Tris-HCl, 0.5% triton, 137.5 mM NaCl, 10% glycerol, 5 mM EDTA supplemented with fresh protease and phosphatase inhibitors. Supernatant represented cytosolic fraction while nuclear pellet was washed twice and lysed in 0.5 Triton X-100 buffer 0.5% SDS and sonicated.

Degradation of Long-Lived Proteins

Sub-confluent cells were incubated with L-U$^{14}$C-serine for 20 h and chased for 1 h with cold media to degrade short-lived proteins. Subsequently cells were incubated with either normal media or starvation media (eventually in the presence of 3-MA) for 4 h. The rate of long-lived protein degradation was calculated from the ratio of soluble radioactivity in the media to that insoluble in the acid-precipitable cell pellet.

RNA Extraction, Reverse Transcription, ChIP and Quantitative PCR

Total RNA was extracted from tissues using TRIzol (Invitrogen) or from cells using RNAesy column (Qiagen). Reverse transcription was performed using TaqMan reverse transcription reagents (Applied Biosystems). Lysosomal and autophagic gene specific primers were previously reported[2]. Autophagy gene primers and mouse primers were purchased from SABiosciences. Fold change calculations were calculated using SABiosciences' online data analysis web site (http://www.sabiosciences.com/per/arrayanalysis.php) which uses the DDC$_t$ method. In brief, the average of the most stable housekeeping genes (GAPDH, ACTB, B2M, RPL13A, HPRT and Cyclophillin) were used as "normalizer" genes to calculate the DC$_t$ value. Next, the DDC$_t$ value is calculated between the "control" group and the "experimental" group. Lastly, the fold change is calculated using $2^{(-DDCt)}$. Biological replicates were grouped to allow calculating the fold change values. Unpaired T-Test was used to calculate statistical significance. Asterisks in the graph indicate that the P-value was <0.05.

Protein Kinase Prediction

Applicants used five methods including CrPhos0.8, GPS-2.1, PhosphoMotifFinder, Networkin and PHOSIDA using the default parameters (15-19). They further filtered CrPhos0.8 and GPS-2.1 predictions according to their confidence scores. For the former, we took into account the predictions with a false positive rate (FPR) equals or less than 30%. For the latter, they considered the predictions with score equals or higher than 5. GPS-2.1 scores were calculated as the difference between actual score and threshold values. We took all the predictions from other three methods. In the case of Networkin, we combined predictions from both Networkin and Networkin 2. Each method describes the kinases associated by S142 site in a different kinase classification, which simply involves four hierarchical levels: kinase group, kinase family, kinase subfamily and kinase itself. To obtain a general consensus in each hierarchical level, we classified each prediction in these four hierarchical levels, if the predictions were not already classified in that manner. They searched for the missing classifications at the http://kinase.org/kinbase database under vertebrate Glade and human species. Consensus in each classification is found according to the majority vote in each classification.

In Vitro Kinase Assay

TFEB-S-142: aa. o 117-166 of Seq Id No. 2: PPPAASPGVRAGHVLSSSAGNSAPNSP-MAMLHIGSNPERELDDVIDNIMR and TFEB-A-142: Seq Id No. 4, corresponding to aa. of 117-166 of Seq Id No. 2 where Ser 142 was substituted with Ala (bold): PPPAASPGVRAGHVLSSSAGNSAPNAP-MAMLHIGSNPERELDDVIDNIMR were synthesized by GENESCRIPT corp. The test peptides TFEB-A-142 and TFEB-S-142 were made up to 1 mM in 50 mM HEPES pH7. There appeared to be no issue with dissolution. The kinase assay was performed at room temperature for 40 minutes at 200 µM ATP and 100 µM of each peptide, using Millipore's standard radiometric assay. All protein kinases were used at their standard KinaseProfiler™ assay concentration. Following incubation, all assays were stopped by the addition of acid and an aliquot spotted onto P30 and Filtermat A to separate products. All tests were carried out in triplicate, and the usual substrate for each protein kinase included as a control.

In Vivo Gene Delivery

The mice were housed in the transgenic mouse facility of Baylor College of Medicine (Houston, Tex., USA). GFP-LC3 transgenic mice were a kind gift of N. Mizushima. C57B6 female mice (4 weeks old) were used, if not otherwise specified. The AAV vector was produced by the TIGEM AAV Vector Core Facility. Briefly, the mouse TFEB (TcFEB) coding sequence was cloned into the pAAV2.1-CMV-GFP plasmid by replacing the GFP sequence and fused in frame with a HA tag. The resulting pAAV2.1-CMV-TcFEB-HA was then triple transfected in sub-confluent 293 cells along with the pAd-Helper and the pack2/9 packaging plasmids. The recombinant AAV2/9 vectors were purified by two rounds of CsCl. Vector titers, expressed as genome copies (GC/mL), were assessed by both PCR quantification using TaqMan (Perkin-Elmer, Life and Analytical Sciences, Waltham, Mass.) and by dot blot analysis. Each mouse was retro-orbital injected with $1.25 \times 10^{11}$ viral particle and sacrificed after 3 weeks. Starved mice were food-deprived for 16 h when analyzed for gene expression, or for 24 h when analyzed for GFP-LC3 dots number.

Histology and Immunofluorescence

Liver samples were collected and fixed overnight in 4% paraformaldehyde in PBS. After cryoprotection in 10 and 30% sucrose in PBS, the specimens were frozen in OCT (Sakura Finetech, Torrance, Calif.) and sectioned 30 µm thick. Images were taken on an Axioplan2 (Zeiss, Thorwood, N.Y.). For immunofluorescence, slices were blocked for 2 h at RT in 2.5% BSA in PBS+0.1% Triton X-100. After blocking, specimens were incubated for 20 h with the primary antibody and, after 3× washes in PBS+0.05% TX-100, for 3 h with secondary antibodies conjugated either with Alexafluor 488 or Alexafluor 555 (Invitrogen). For immunohistochemistry analyses of HA the avidin-biotin complex (ABC) method was used (Vectastain Elite ABC kit). Anti-GFP was from Abcam; (diluition 1:500)

Electron Microscopy

Control and TFEB-overexpressing cells were washed with PBS, and fixed in 1% glutaraldehyde dissolved in 0.2 M Hepes buffer (pH 7.4) for 30 min at room temperature. The cells were then postfixed for 2 h in OsO4. After dehydration in graded series of ethanol, the cells were embedded in Epon 812 (Fluka) and polymerized at 60° C. for 72 h. Thin sections were cut at the Leica EM UC6, counterstained with uranyl acetate and lead citrate. EM images were acquired from thin sections using a Philips Tecnai-12 electron microscope equipped with an ULTRA VIEW CCD digital camera (Philips, Eindhoven, The Netherlands). Quantification of vacuolization was performed using the AnalySIS software (Soft Imaging Systems GmbH, Munster, Germany). Selection of cells for quantification was based on their suitability for stereologic analysis, i.e. only cells sectioned through their central region (detected on the basis of the presence of Golgi membranes) were analyzed.

Animal Models

All procedures involving mice were approved by the Institutional Animal Careand Use Committee of the Baylor College of Medicine. GFP-LC3 transgenic line was described previously. Tissue specific overexpression of Tcfeb was generated as follows: Tcfeb-3×Flag cDNA was inserted after a CAGCAT cassette [chicken actin promoter (CAG) followed by chloramphenicol acetyltransferase (CAT) cDNA flanked by 2 loxP sites] and used to generate transgenic mice (Baylor College of Medicine transgenic core). Mice were then crossed with Albumin-CRE (obtain from the Jackson laboratory) line. For 48 Starvation protocol the mice were food deprived for 22 h, subsequently were fed for 2 h and fasted again for 24 h prior sacrifice.

Enzymatic Activities

Lysosomal enzymes acid phosphatase, beta-galactosidase, and beta-hexosaminidaseactivities were measured using the appropriate fluorimetric or colorimetric substrates. SGSH activity was measured following protocols described in Fraldi et al., *Hum Mol Gen* 2007 (33).

Immunoblotting and Antibodies

The mouse anti-TFEB monoclonal antibody was purchased from My Biosource catalogue No. MBS120432. To generate anti-pS142 specific antibodies, rabbits were immunized with the following peptide coupled to KLH: AGNSAPN{pSer}PMAMLHIC. Following the fourth immunization, rabbits were sacrificed and the serum was collected. Non-phosphospecific antibodies were depleted from the serum by circulation through a column containing the non-phosphorylated antigene. The phosphospecific antibodies were subsequently purified using a column containing the phosphorylated peptide. Cells were lysed with M-PER buffer (Thermo) containing protease and phosphatase inhibitors (Sigma); nuclear/cytosolic fractions were isolated as above described. Proteins were separated by SDS-PAGE (Invitrogen; reduced NuPAGE 4-12% Bis-tris Gel, MES SDS buffer). If needed, the gel was stained using 20 ml Imperial Protein Stain (Thermo Fisher) at room temperature for 1 h and de-stained with water. Immunoblotting analysis was performed by transferring the protein onto a nitrocellulose membrane with an I-Blot (Invitrogen). The membrane was blocked with 5% non-fat milk in TBS-T buffer (TBS containing 0.05% Tween-20) and incubated with primary antibodies anti-FLAG and anti-TUBULIN (Sigma; 1:2000), anti-H3 (Cell Signaling; 1:10 000) at room temperature for 2 h whereas the following antibodies were incubated ON in 5% BSA: anti-TFEB (My Biosource; 1:1000), anti-P TFEB (1:1000) ERK1/2, p-ERK1/2, p-P70S6K, P70S6K (Cell Signaling; 1:1000). The membrane was washed three times with TBS-T buffer and incubated with alkaline phosphatase-conjugated IgG (Promega; 0.2 mg/ml) at room temperature for 1 h. The membrane was washed three times with TBS buffer and the expressed proteins were visualized by adding 10 ml Western Blue Stabilized Substrate (Promega).

High Content Nuclear Translocation Assay

TFEB-GFP cells were seeded in 384-well plates, incubated for 12 hours, and treated with ten different concentrations (50000 nM, 16666.66 nM, 5555.55 nM, 1851.85 nM, 617.28 nM, 205.76 nM, 68.58 nM, 22.86 nM, 22.86 nM, 7.62 nM, and 2.54 nM) of ERK inhibitor U0126 (Sigma-Aldrich) and mTOR inhibitors Rapamycin (Sigma-Aldrich), Torin 1 (Biomarin), and Torin 2 (Biomarin). After 3 hours at 37° C. in RPMI medium cells were washed, fixed, and stained with DAPI. For the acquisition of the images, ten pictures per each well of the 384-well plate were taken by using confocal automated microscopy (Opera high content system, Perkin Elmer). A dedicated script was developed to perform the analysis of TFEB localization on the different images (Acapella software, Perkin Elmer). The script calculates the ratio value resulting from the average intensity of nuclear TFEB-GFP fluorescence divided by the average of the cytosolic intensity of TFEB-GFP fluorescence. The results were normalized using negative (RPMI medium) and positive (HBSS starvation) control samples in the same plate. The data are represented by the percentage of nuclear translocation at the different concentrations of each compound using Prism software (GraphPad software). The EC50 for each compound was calculated using non-linear regression fitting (Prism software).

Results

TFEB Induces Autophagy (Macro)autophagy is an evolutionary conserved mechanism that targets intracytoplasmic material to lysosomes, thus providing energy supply during nutrient starvation (1, 3). Autophagy activation during starvation is regulated by mTOR, whose activity is dependent on cellular energy needs.

Figure 1:
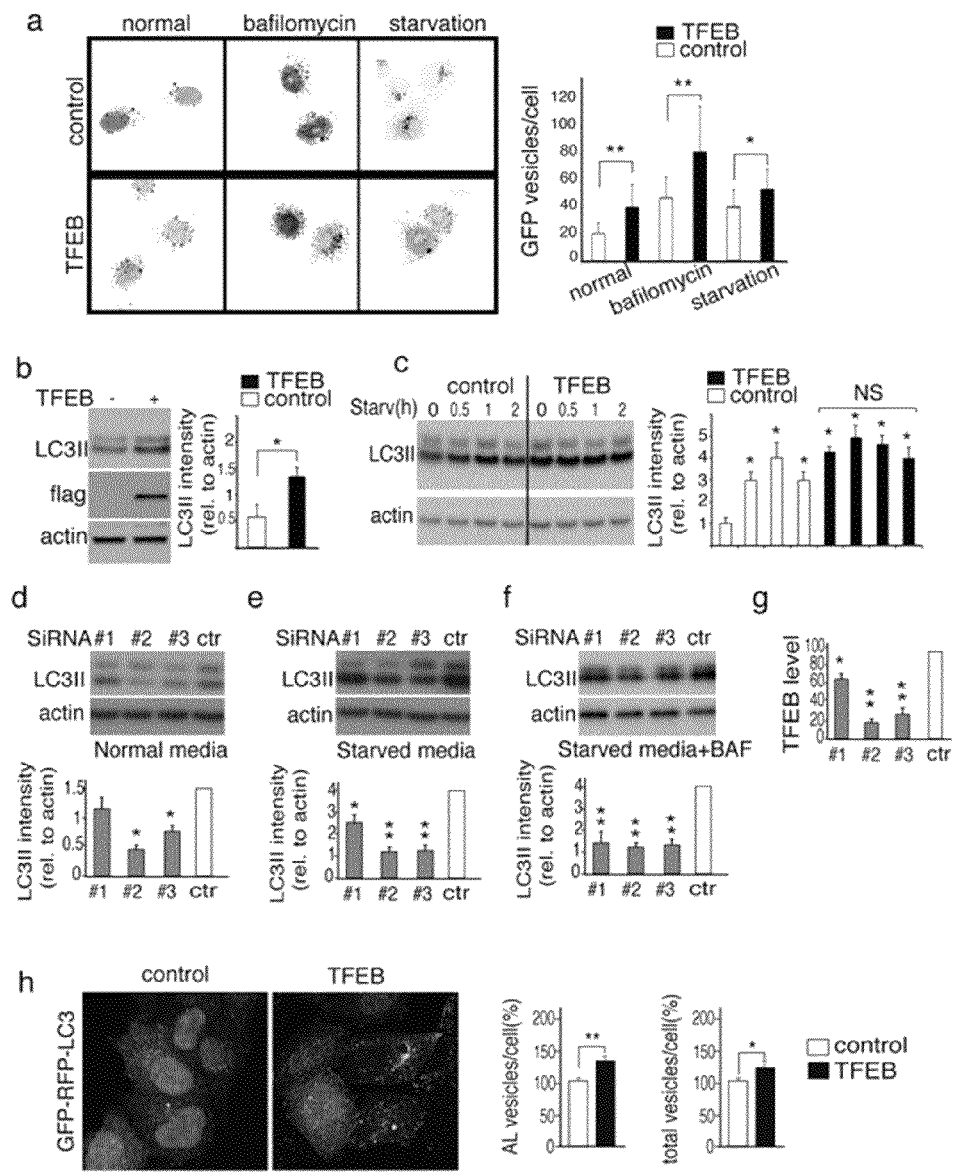
FIG. 1 TFEB induces autophagy. (A) HeLa cells stably overexpressing TFEB were transfected with a GFP-LC3 plasmid and treated as indicated. Approximately 100 cells were analyzed in triplicate for each experiment. The graph shows quantification of GFP-positive vesicles. (B-F) Western blot analysis of LC3 in (B) TFEB-3×flag stable overexpressing (+) and control cells (−). The graph represents the quantification using imageJ software analysis of LC3II expression (relative to actin) from three independent blots; (C) TFEB stable overexpressing cells, which were serum and amino acid-starved (Starv) for the indicated time (h=hours), (D-F) cellular lysates isolated from TFEB-RNAi and control cells treated with scrambled RNAi (ctr) cultured in (D) normal media, (E) starved media, or (F) starved media supplemented with bafilomycin (4 h; 400 nM). The graph represents the quantification of LC3II expression (relative to actin) from three independent blots and band intensities were quantified using imageJ software analysis. (G) TFEB mRNA levels were analyzed by qPCR using cDNAs prepared from cells transfected with 3 different siRNA oligos targeting TFEB (oligo #1, #2, #3), or with a scrambled siRNA oligo (ctr). (H) Representative confocal images of fixed HeLa cells stably expressing GFP-mRFP-LC3 transfected with empty (control) or TFEB vector. A minimum of 2000 cells was counted and the values represent the average number of vesicles (relative to the control, %) obtained from three independent experiments. AL (autolysosomes)=mRFP positive/GFP negative vesicles; total: mRFP positive vesicles. (All error bars represent standard deviations. T-test (unpaired)p value (*)<0.05, (**)<0.01)
Figure 5:
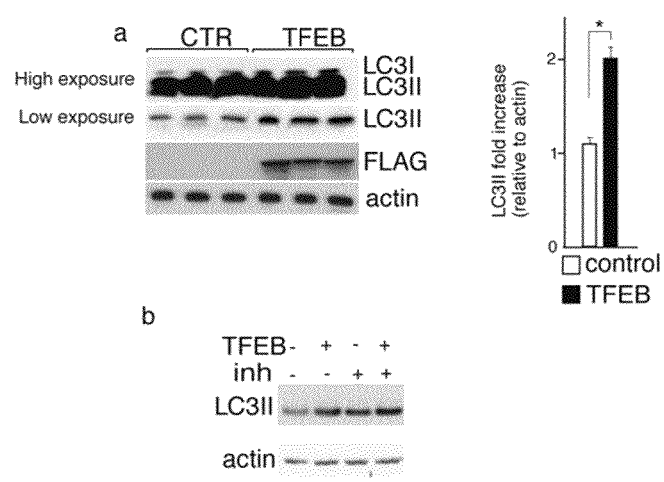
FIG. 5 TFEB transient overexpression induces autophagy. (A) HeLa cells were transiently transfected with a plasmid encoding for flagged TFEB protein. 48 h after transfection cells were collected, lysed and 10 mg of protein samples were analyzed for LC3, Flag and actin immunoreactivity. Experiments were performed in triplicate and band intensities were quantified using imageJ software analysis (Error bars represent standard deviations. p value (*)<0.05) (B) COS-7 cells were transiently transfected with an empty vector or with a TFEB-3xFlag vector. 24 hours later cells were treated for 4 h with lysosomal inhibitors (pepstatin/E64, 10 μg/ml, SIGMA). 10 μg of cell lysates were subjected to LC3 and actin immunoblotting.
Figure 6:
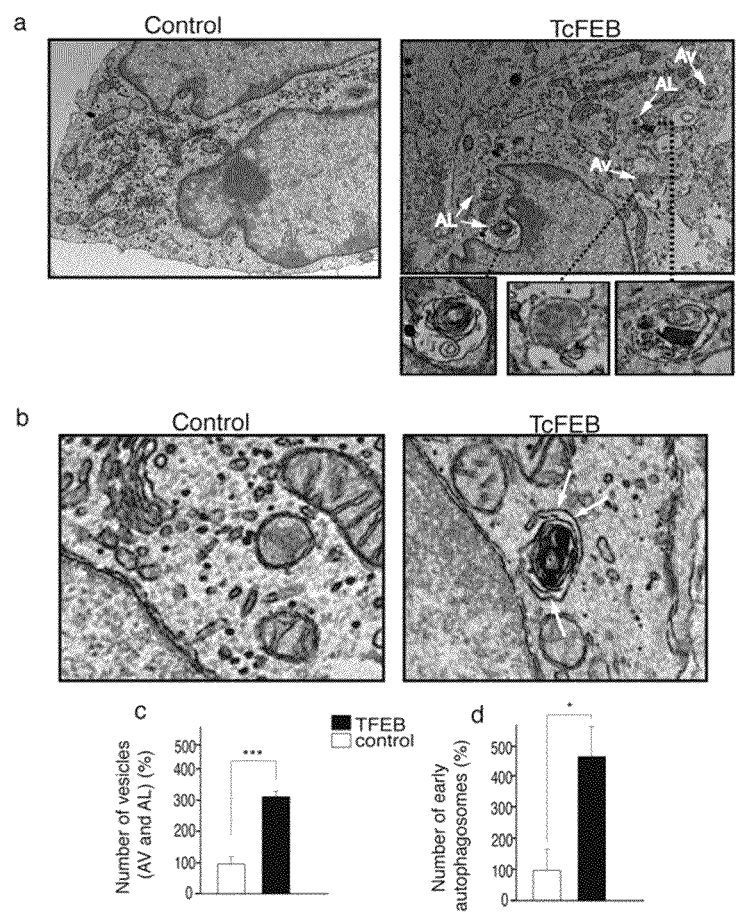
FIG. 6 Induction of autophagy in TcFEB overexpressing MEFs. (A,B) Electron micrograph of MEFs infected with lentivirus expressing TcFEB and control cells. (a) Autophagic structures were observed upon TcFEB expression, including autophagosomes (AV) and autolysosomes (AL). (B) Formation of early autophagosome. Isolation membrane (arrows) surrounding electron-dense cytoplasmatic material. (C) Quantitation of number of autophagic structure (AV and AL) and (D) of early autophagosomes. At least 30 cells/group were analyzed. Error bar represent SEM; p value (*)<0.05; (***)<0.0001.
Figure 7:
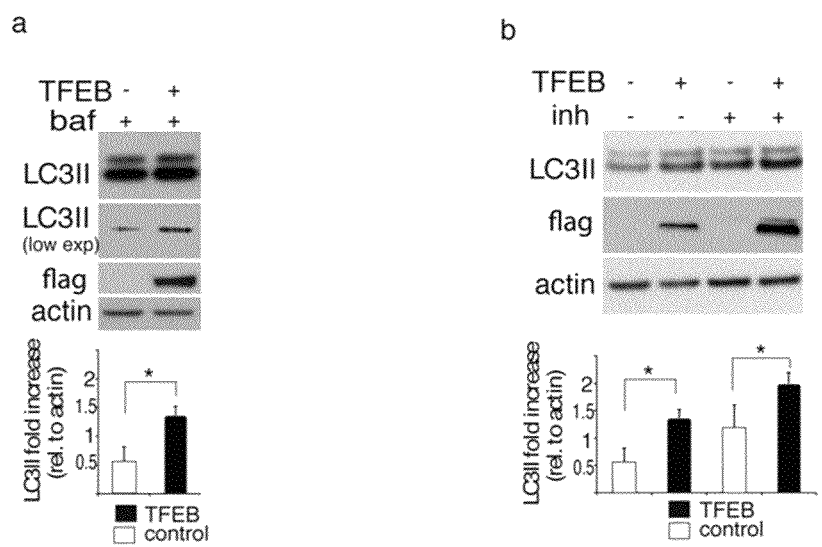
FIG. 7 TFEB promotes autophagosome formation. (A) Control and stable TFEB-overexpressing cells were treated with bafilomycin (baf; 12 h 400 nM) harvested and subjected to LC3II, Flag and actin immunoblotting. (B) Control and TFEB-overexpressing cells were left untreated or treated with 10 μg/ml lysosomal inhibitor pepstatin/E64 for 4 h, lysed and subjected to LC3, Flag and actin immunoblotting. Experiments were performed in triplicate and band intensities were quantified using imageJ software analysis (Error bars represent standard deviations. p value (*)<0.05).

As autophagy is the result of a tight partnership between autophagosomes and lysosomes (1), applicants tested whether TFEB, a transcription factor that controls lysosomal biogenesis, regulated autophagy. As TFEB exerts a positive control on lysosomal biogenesis and function (2) and on lysosomal exocytosis (FIGS. 16 and 17), one would expect that TFEB overexpression should decrease the number of autophagosomes due to their increased degradation by the lysosomes. Surprisingly, stable TFEB overexpression in HeLa cells increased significantly the number of autophagosomes, as determined by using the LC3 marker, which specifically associates with autophagosomes (4-7) (FIG. 1a,b). Similar data were obtained by transient overexpression of TFEB in HeLa and Cos cells (FIG. 5). An increase in the number of autophagosomes was also detected by electron microscopy on mouse embryonic fibroblast (MEFs) infected with a lentivirus overexpressing TFEB (FIG. 6). This increase persisted in cells treated with lysosomal inhibitors of autophagosome/LC3II degradation bafilomycin and pepstatin/E64 (8), indicating that TFEB activates the formation of autophagosomes (FIG. 1a and FIG. 7). Nutrient starvation did not further increase the number of autophagosomes in TFEB-overexpressing cells (FIG. 1a,c), suggesting a saturating effect of TFEB overexpression on autophagy and raising the possibility that TFEB may be an important mediator of starvation-induced autophagy.

Figure 8:
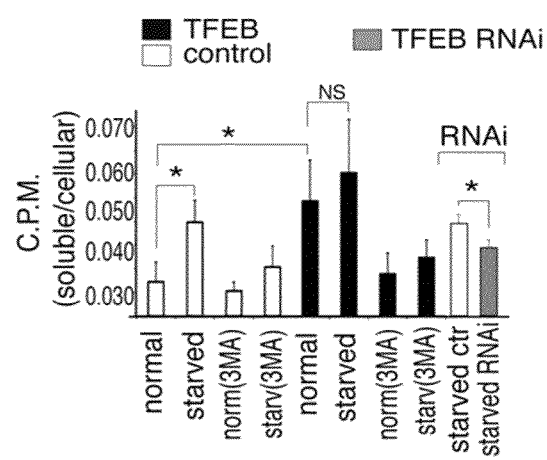
FIG. 8 TFEB increases autophagic proteolysis. Rate of long-lived protein degradation in TFEB-overexpressing, TFEB-depleted and control cells in either normal or starved condition. 3-methyl adenine (3MA) was added where indicated (Error bars represent standard deviations. p value (*)<0.05).

Consistent with these findings, RNA interference (RNAi) of TFEB in HeLa cells resulted in decreased levels of LC3II both in normal and starved conditions, either in the presence or absence of bafilomycin (FIG. 1d-f). Notably, the decrease of LC3II correlated with the levels of TFEB downregulation achieved by the different RNAi oligos, demonstrating the specificity of the assay (FIG. 1g). These gain and loss of function data suggest that the biogeneses of autophagosomes and lysosomes are co-regulated by TFEB. Applicants next measured the rate of delivery of autophagosome to lysosome using an RFP-GFP tandem tagged LC3 protein (9), which discriminates early autophagic organelles (GFP-positive/ mRFP-positive) from acidified autolysosomes (GFP-negative/mRFP-positive), as the GFP signal (but not the mRFP) is quenched inside acidic compartments (9). They found that the number of autophagolysosomes was higher in TFEB overexpressing cells compared to control cells, indicating that TFEB promotes autophagosome-lysosome fusion, thus enhancing the autophagic flux (FIG. 1h). Functional evidence of TFEB role in the regulation of autophagy came from the observation that degradation of long-lived proteins was enhanced by TFEB overexpression, and reduced by TFEB knock-down. This enhancement was abolished by the autophagy inhibitor 3-methyl adenine (3-MA)(10) (FIG. 8).

Figure 9:
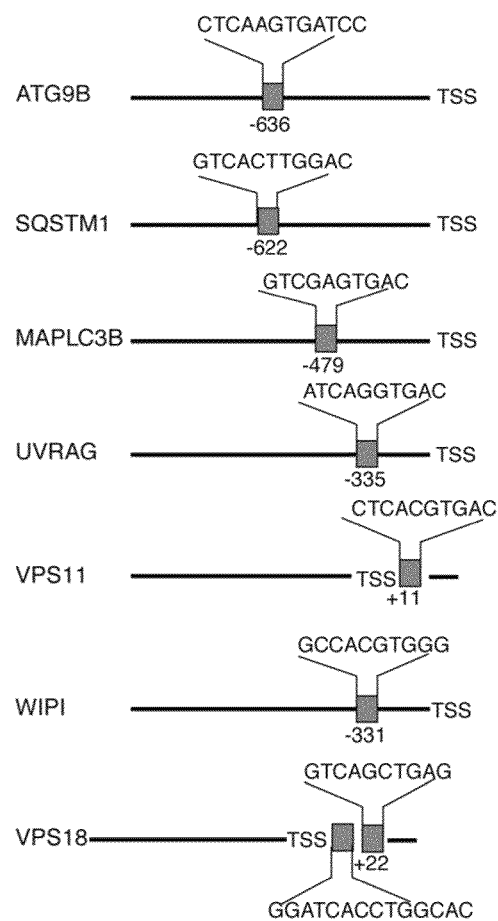
FIG. 9 Distribution of the TFEB putative binding elements in the promoter regions of a subset of autophagy genes. Numbers indicate the distance of the binding element from the transcription start site (TSS).

To test whether TFEB regulated the expression of autophagy genes, applicants analyzed the mRNA levels of a group of 51 genes reported to be involved in several steps of the autophagic pathway (1, 12, 13). They observed that the enhancement of the expression levels of autophagy genes in cells overexpressing TFEB was very similar to the one obtained during starvation (HeLa cells 4h in EBSS media) (Pearson correlation: r value=0.42; pvalue=0.001), while they were downregulated after TFEB silencing (FIG. 2a and Tables 1 and 2). Among them the expression of UVRAG, WIPI, MAPLC3B, SQSTM1, VPS11, VPS18 and ATG9B was most significantly affected by TFEB overexpression (Tables 1 and 2). These genes are known to play a role in different steps of autophagy and appeared to be direct targets of TFEB, as they carry at least one CLEAR site (2) in their promoters (FIG. 9). Interestingly, VPS11, VPS18 and UVRAG play roles in autophagosome delivery to lysosomes (14), consistent with the observation of a significant enhancement of lysosome-autophagosome fusion in cells overexpressing TFEB.

Figure 10:
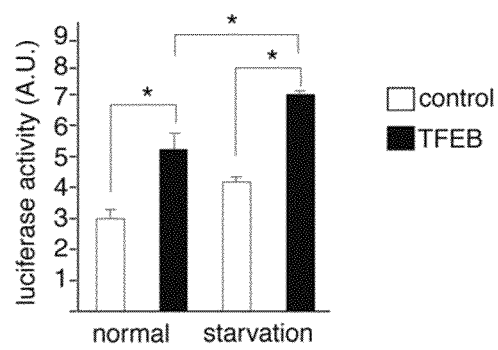
FIG. 10 Starvation enhances TFEB activity. Luciferase report assay using a construct carrying four tandem copies of TFEB binding sites. Both normal and TFEB-overexpressing HeLa cells were transfected with an artificial promoter with TFEB binding sites. Both cells types displayed increased transactivation potential when cultured in starved conditions. (Error bars represent standard deviations p (*)<0.05)

These data indicate that TFEB is involved in the transcriptional regulation of starvation-induced autophagy. This conclusion is strongly bolstered by the following observations. First, the luciferase reporter assay (2) showed that starvation enhanced the effects of TFEB on target gene transcription (FIG. 10). Second, the expression of TFEB direct targets was upregulated in starved cells and this upregulation was inhibited by TFEB silencing (FIG. 2a,c).

Starvation Regulates TFEB Nuclear Translocation and Activity

Figure 11:
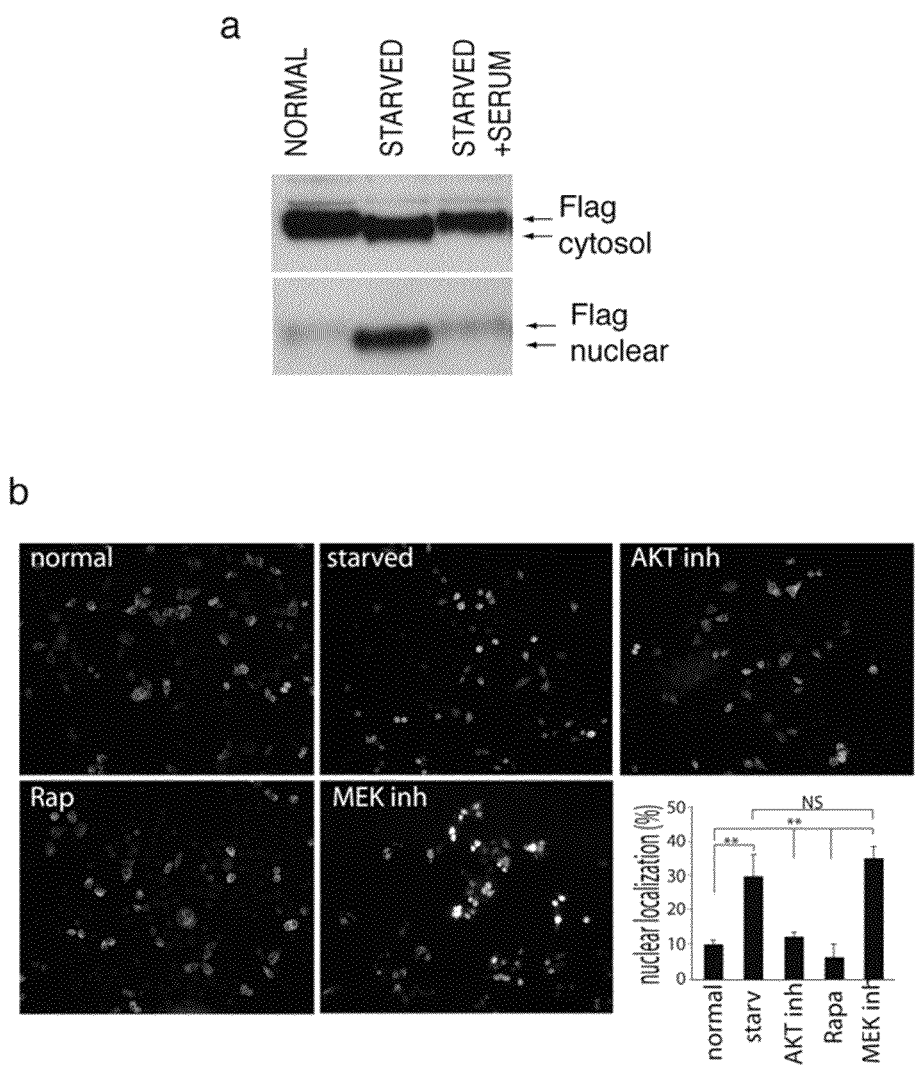
FIG. 11 Starvation induces TFEB nuclear translocation through MAPK. (A) Starvation induces cytosolic TFEB mobility shift and nuclear translocation. Normal medium; starved medium (4 h); starved+normal, indicates that cell were cultured in starved medium (4 h) and supplemented with normal medium 1 h prior to harvesting. Cytosolic and nuclear fractions were subjected to Flag immunoblotting. (B) Analysis of TFEB cellular localization by immunofluorescence in HeLa cells treated as indicated in FIG. 2G. The graph shows percentage of cells that display TFEB nuclear localization. Error bars represent standard deviations. P value (*)<0.05

To identify the mechanism of starvation-induced activation of TFEB applicants analyzed its subcellular localization and post-translational modifications in starved cells. In normal conditions TFEB is localized to the cytoplasm (2). They observed that nutrient starvation (EBSS media) rapidly induced TFEB nuclear translocation (FIG. 2d,e), and that cytosolic TFEB from starved cells appeared to have a lower molecular weight compared to that of normally fed cells, as revealed by western blot analysis (FIG. 11a). This molecular weight shift occurred rapidly but transiently and was abolished within 1 h after re-adding normal media to starved cells, concomitant with a decrease of nuclear TFEB (FIG. 11a). By supplementing EBSS media either with serum, amino acids or growth factors (i.e. insulin or EGF) applicants observed a significant inhibition of TFEB nuclear translocation compared to starved media alone (FIG. 2f). Almost no effect was observed when EBSS was supplemented with cytokines (i.e. INF or LIF) (FIG. 2f), suggesting that activation of TFEB is a process regulated by a signaling mechanism, which is sensitive to nutrient and growth factors. Applicants stimulated starved cells with normal medium supplemented with drugs inhibiting the mTOR (Rapamycin), PI3K-AKT (Triciribin)

and MEK (U0126) kinases. MEKi-inhibition resulted in TFEB nuclear localization, at level similar to starvation, while AKT and mTOR inhibition had no effect (FIG. 2g and FIG. 11b). These data suggest that TFEB activity is regulated by MAP kinase, uncovering an unexpected role of this signaling pathway in the regulation of starvation-induced autophagy. Furthermore, the expression of a constitutively active MEK (caMEK) in HeLa cells resulted in downregulation of TFEB target gene expression during starvation, thus mimicking the effect of TFEB knockdown (FIG. 2h), while caMEK overexpression in TFEB-depleted cells had no effect on the expression of TFEB target genes (FIG. 2h).

Serine Phosphorylation Regulates TFEB Activation

Figure 3:
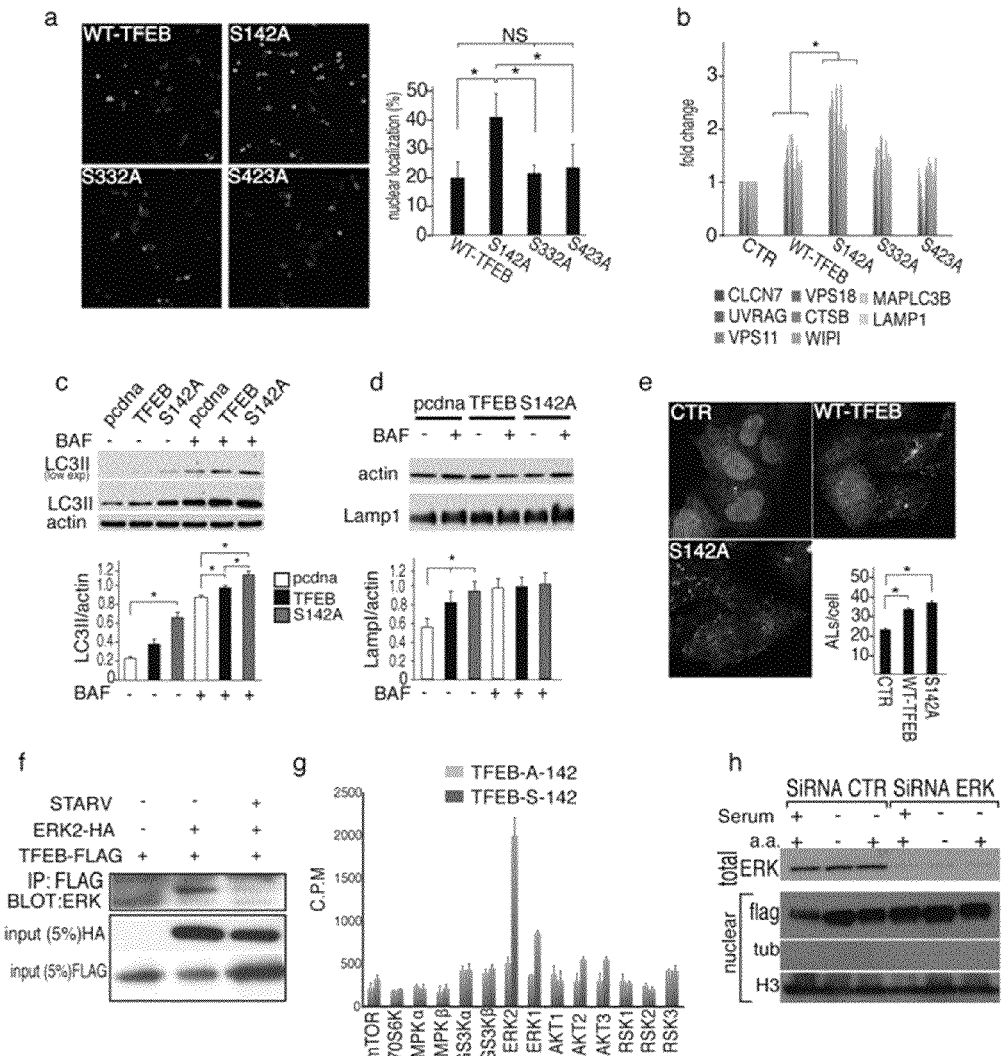
FIG. 3 Serine phosphorylation regulates TFEB activation. (A) TFEB subcellular localization in HeLa cells expressing mutated versions of TFEB-3×Flag, immunostained with Flag antibody. Five fields from three independent experiments, containing 50-100 cells each were analyzed. (B) qPCR analysis of TFEB target gene expression 24 h post-transfection with empty, normal and mutant TFEB plasmids. (C,D) Western blot analysis of LC3II (C) and Lamp1 (D) in protein extracts from HeLa cells transfected with equal amounts of empty (pcDNA), TFEB-3×Flag or TFEBS142A-3×Flag vectors. Bafilomycin was added where indicated. Experiments were done in triplicate and the quantification of proteins levels were normalized to actin levels. (E) Analysis of autolysosomes (AL=RFP positive/GFP negative) in HeLa cells stably expressing GFP-mRFP-LC3 and transfected with either pcDNA, Tfeb or Ser-Tfeb for 24 h. Quantification as reported in FIG. 1H. (F) Western blot analysis using anti-Erk antibody on HeLa cells transfected with HA-Erk2 kept and/or TFEB-3×Flag, kept in full serum or nutrient starved for 4 h and immunoprecipitated with anti-Flag antibody. Lysates were immunoprecipitated with anti-FLAG and blotted with an anti-Erk antibody. (G) In vitro kinase assay. Recombinant kinases were incubated in the presence of ATP-$\gamma$ $^{32}$P and of a peptide spanning from amino acid 120 to 170 of TFEB protein (TFEB-S-142) or with a similar peptide in which serine 142 was substituted with alanine (TFEB-A-142). Phosphorylation efficiency ("phosphorylation sensitivity") was measured as the amount of radioactivity incorporated by the peptides. (H) HeLa stable clones overexpressing TFEB were transfected with siRNA oligonucleotides specific for ERK1/2 or with control siRNA. 48 h later cells were left untreated, serum starved or serum and amino acid (a.a.) starved for 4 h, harvested and subjected to nuclear isolation and Flag immunoblotting. Total lysates were probed with ERK antibody. All error bars represent standard deviations. P value (*)=<0.05.
Figure 12:
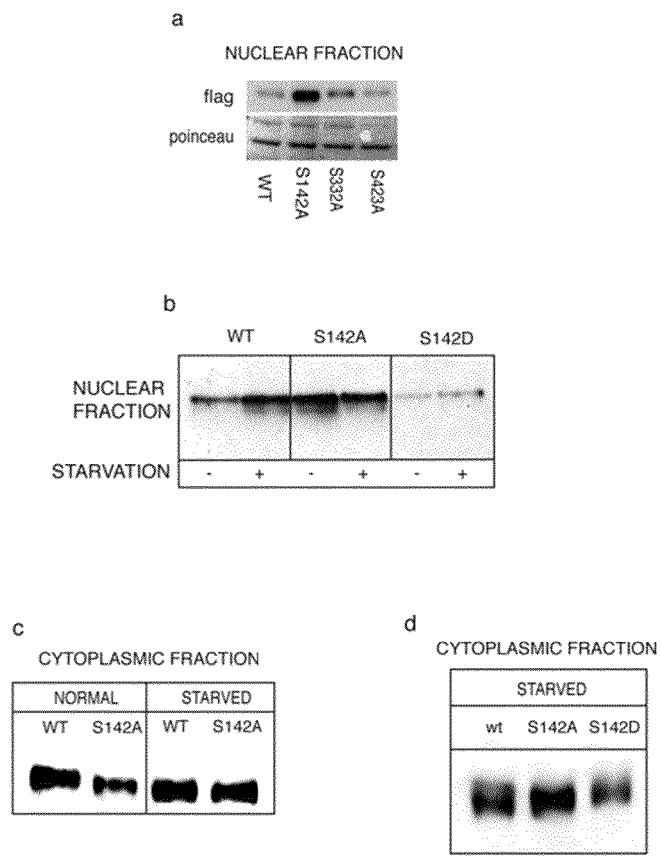
FIG. 12 TFEB nuclear translocation is dependent on S142 phosphorylation. (A) HeLa cells expressing TFEB-3xFlag, S142A-3xFlag, S332-3xFlag or S423-3xFlag proteins were subjected to nuclear protein isolation. Equal amounts of nuclear proteins were verified by ponceau staining. (B) HeLa cells expressing TFEB-3xFlag, S142A-3xFlag and S142D-3xFlag proteins were subjected to nuclear protein isolation in normal and in starved conditions. (C) Flag immunoblotting of cytosolic protein isolated from HeLa cells expressing TFEB-3xFlag and TFEB-S142A-3xFlag showing that in normal media S142A migrates as lower MW band compared to WT TFEB while this shift is not evident anymore in starved conditions. (D) Flag immunoblotting of cytosolic protein isolated from starved HeLa cells expressing TFEB-3xFlag, S142A-3xFlag and S142D-3xFlag showing a reduced shift of TFEB-S142D.
Figure 13:
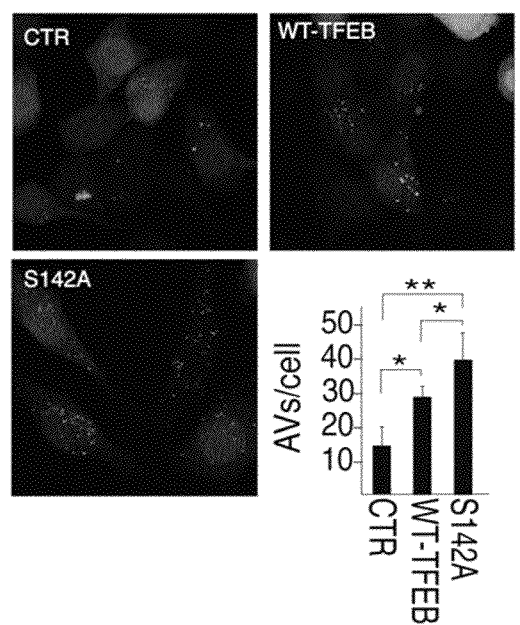
FIG. 13 S142A TFEB mutant displays enhanced activity. HeLa cells stably overexpressing GFP-LC3 were transfected with equal amounts of empty, TFEB-3xFlag or S142A-TFEB-3xFlag plasmids and the number of autophagosomes was quantified. At least ten fields (containing 4-10 cells) were analyzed for each point. Experiments were performed in triplicate. Error bars represent standard deviations. p value (*)<0.05.

To analyze more in detail the relationship between MAPK signaling and TFEB applicants performed a mass-spectrometry analysis and identified at least three serines (i.e. S142, S332, and S402) that were phosphorylated in nutrient rich medium but not in starved medium. They mutated each of these three serines to alanines to abolish phosphorylation. Mutant TFEB proteins were individually expressed into HeLa cells and TFEB nuclear translocation analyzed. The TFEB(S142A) mutant showed a significantly increased nuclear localization compared to TFEB(WT), TFEB(S332A) and TFEB(S402A) (FIG. 3a and FIG. 12a). Conversely the phospho-mimetic mutant (TFEB S142D) was unable to translocate into the nucleus upon nutrient starvation (FIG. 12b). The S142A TFEB mutant migrates at lower molecular weight in normal but not in starved media, while the S142D mutant displayed a reduced shift during starvation compared to WT TFEB (FIG. 12c,d), further demonstrating that S142 is phosphorylated in normal but not in starved media. The expression of TFEB(S142A) resulted in increased expression levels of TFEB target genes compared to TFEB(WT), TFEB(S332A) and TFEB(S402A) (FIG. 3b). Consistently, TFEB(S142A) caused a stronger induction of the autophagic/lysosomal system, compared to wt TFEB, as demonstrated by the increased number of autophagosomes (FIG. 3c and FIG. 13), lysosomes (FIG. 3d) and autophagolysosomes (FIG. 3e). Thus, TFEB nuclear translocation and activation are regulated by the phosphorylation of serine 142.

To identify the specific kinase responsible for the phosphorylation of serine 142, applicants performed bioinformatic analyses using methods that are based on computational models built upon a set of experimentally validated phosphorylation sites (15-19) (see methods for details). Consistently with previous results, they identified the serine-specific Extracellular Regulated Kinases (ERKs) as the top-ranking candidates for the phosphorylation of serine 142 (Table 3). Interestingly, serine 142 is highly conserved in other members of the HLH-leucine zipper gene family, such as the Microphthalmia Transcription Factor (MITF) (FIG. 14), where it was found to be phosphorylated by ERK2 (20). Further evidence of ERK2-mediated TFEB phosphorylation came from ERK2-TFEB co-immunoprecipitation (FIG. 3f) in normal but not in starved media Furthermore siRNA-mediated knock-down of ERK1/2 proteins induced TFEB nuclear translocation to a similar extent as nutrient starvation (FIG. 3h).

In Vivo Analysis of TFEB-Mediated Induction of Autophagy

Figure 4:
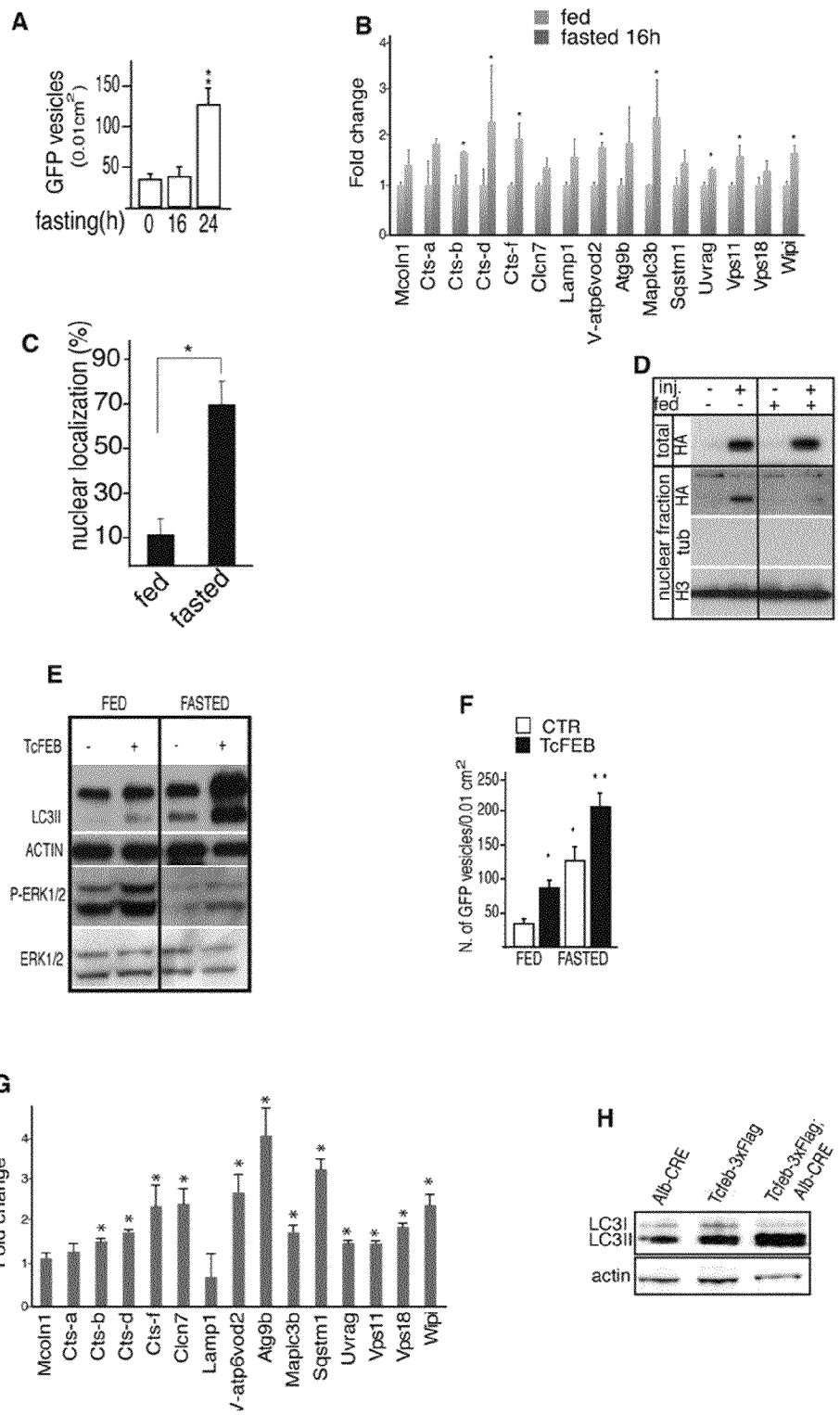
FIG. 4 In vivo analysis of TFEB-mediated induction of autophagy. (A) Immunofluorescence analysis of GFP-positive vesicles in fed, 16 h-fasted, and 24 h-fasted mice. Quantification of vesicles is shown in the graph. (B) qPCR analysis of TFEB target gene expression in liver samples from fed and fasted animals (n=3; Error bars represent standard deviations. p value (*)<0.05). Gapdh and Hprt were used as reference genes. (C,D) Analysis of TFEB subcellular localization in two month-old wild type mice infected with AAV2/9Tcfeb-HA and fasted 16 h prior to sacrifice. (C) HA-immunofluorescence analysis. The graph shows quantification of nuclear HA signal. 100 transduced cells were counted for each liver. n=3 mice/group. *=<0.001. (D) Western blot analysis of HA, Tubulin and H3 in liver specimens subjected to nuclear fractionation. Total liver lysates were probed with an HA antibody to verify comparable transgene expression between fed and fasted animals. (E) Western blot analysis of LC3, actin, p-ERK1/2 and ERK1/2 in liver extracts from mice injected AAV2/9Tcfeb-HA. (F) Western blot analysis of GFP and DAPI staining in cryopreserved liver slices from 2-month old GFP-LC3 transgenic mice injected with either AAV-Tcfeb-HA or with saline solution (control group) and fed ad libitum or fasted for 24 h prior sacrifice. Quantification of GFP-positive vesicles is shown in the graph. (G) qPCR analysis of both autophagic and lysosomal TFEB-target gene expression in liver samples isolated from conditional Tcfeb-3xFLAG transgenic mice (Tcfeb-3xflag;AlbCRE), in which transgene expression is driven by a liver-specific CRE recombinase (i.e. Albumin-CRE). (H) Western blot analysis of LC3 and actin in liver protein extracts from Alb-CRE, Tcfeb-3xFlag and Tcfeb-3xFlag; Alb-CRE mice.

Applicants analyzed the physiological relevance of TFEB-mediated control of the lysosomal/autophagic pathway in vivo in GFP-LC3 transgenic mice (11). They focused studies on the liver, due to the reported autophagic response observed in liver upon nutrient depletion. In liver, the number of GFP-positive vesicles started to increase after 24 hrs of fasting, and peaked at 48 hrs (see mat and methods for 48 h starvation protocol) (FIG. 4a), while the transcriptional induction of both autophagic and lysosomal TFEB target genes was evident after 16 hrs of fasting (FIG. 4b). Therefore, transcriptional activation precedes autophagosome formation in vivo. Importantly, at 16 hrs of fasting the sub-cellular localization of TFEB was completely nuclear (FIG. 4c,d) and the level of ERK phosphorylation was reduced compared to fed animals (FIG. 4e), indicating that starvation regulates TFEB activity in vivo, similarly to what was observed in cultured cells.

Figure 15:
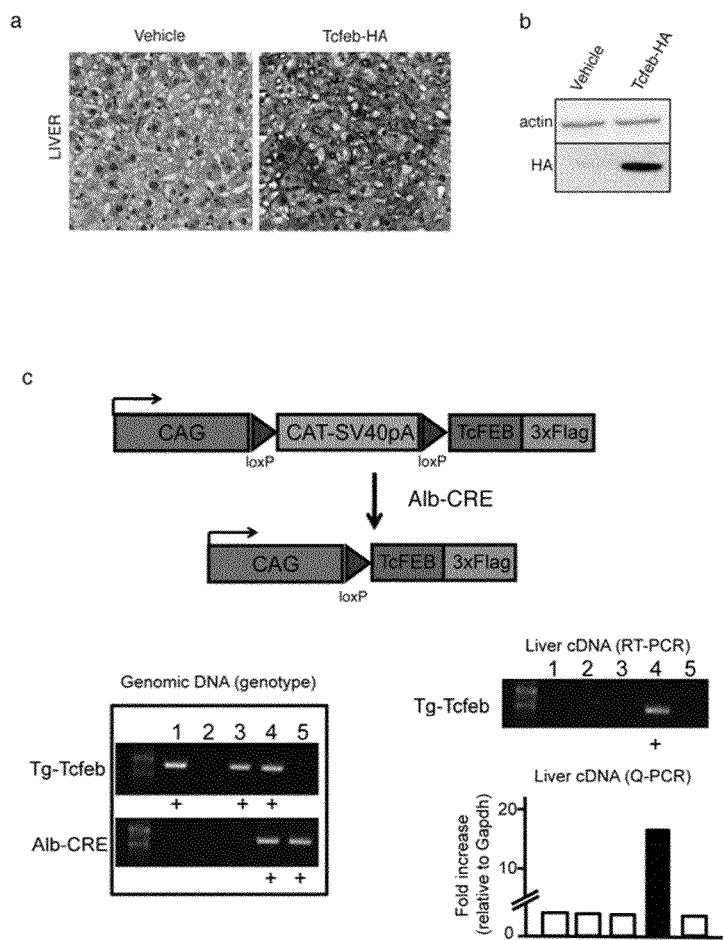
FIG. 15 Strategy for TcFEB overexpression in vivo. (A) Representative images of cryopreserved liver slices immunostained with anti-HA antibody (to verify viral transduction efficiency). (B) Liver protein extracted from Tcfeb-HA injected and control mice were immunoblotted HA and actin antibodies. (C) Generation of a transgenic mouse line for TcFEB conditional overexpression. The map of the transgene vector, before and after CRE recombinase is illustrated at the top. Representative genotypes of littermates are shown on the left, while the correspondent liver-specific TFEB overexpression in mouse n4 is shown on the right.

Applicants evaluated if TFEB was sufficient to induce autophagy in vivo using both viral- and transgene-mediated TFEB overexpression. GFP-LC3 transgenic mice (11) were injected systemically with an adeno-associated viral (AAV) vector containing the murine TcfebcDNA tagged with an HA epitope (AAV 2/9-Tcfeb-HA) (FIG. 15a,b). Liver specimens from Tcfeb-injected animals showed a significant increase in the number of GFP positive vesicles, and this increase was further enhanced by starvation (FIG. 4e,f). In addition, liver samples from conditional Tcfeb-3xFLAG transgenic mice, in which transgene expression is driven by a liver-specific CRE recombinase (i.e. Albumin-CRE) (FIG. 15c), displayed a significant increase in the expression of lysosomal and autophagic genes and in the number of autophagosomes compared to control littermates (FIG. 4g,h). Together, these data point to an important role of TFEB in the transcriptional regulation of starvation-induced autophagy.

TORC1 Regulates TFEB Subcellular Localization

Figure 18:
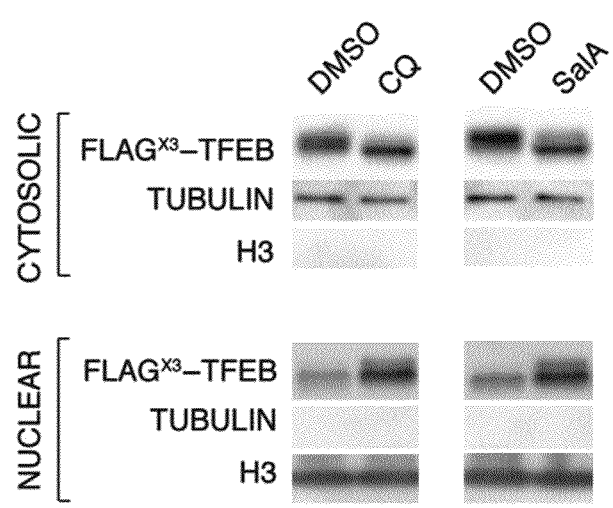
FIG. 18 Lysosomal stress induces TFEB nuclear translocation. Immunoblotting of proteins extracted from HeLa cells that express TFEB-3×Flag treated with chloroquine (CQ) or Salicylihalamide A (SalA), subjected to nuclear/cytosolic fractionation and blotted with antibody against FLAG to detect TFEB. Histone 3 (H3) and tubulin were used as nuclear and cytosolic markers, respectively. Blots are representative of triplicate experiments.

TFEB subcellular localization was then analysed in HeLa and HEK-293T cells transiently transfected with a TFEB-3x FLAG plasmid and treated overnight with inhibitors of lysosomal function. These treatments included the use of chloroquine, an inhibitor of the lysosomal pH gradient, and Salicylihalamide A (SalA) a selective inhibitor of the v-ATPase (38). Immunoblotting performed after nuclear/cytoplasmic fractionation revealed that also lysosomal stress induced nuclear translocation of exogenously expressed TFEB and that again TFEB nuclear accumulation was associated with a shift of TFEB-3xFLAG to a lower molecular weight, suggesting that lysosomal stress may affect TFEB phosphorylation status (FIG. 18).

Based on the observation that mTORC1 resides on the lysosomal membrane and its activity is dependent on both nutrient and lysosomal function (39, 40), applicants postulated that the effects of lysosomal stress on TFEB nuclear translocation may be mediated by mTORC1. Consistent with this idea, chloroquine or SalA inhibited mTORC1 activity as measured by level of p-P70S6K, a known mTORC1 substrate (FIG. 19A), (40). The involvement of mTOR appears in contrast with our previous observation that Rapamycin, a known mTOR inhibitor, did not affect TFEB activity. However, recent data indicate that Rapamycin is a partial inhibitor of mTOR, as some substrates are still efficiently phosphorylated in the presence of this drug (41). Therefore, applicants used kinase inhibitors Torin 1 and Torin 2, which belong to a novel class of molecules that target the mTOR catalytic site, thereby completely inhibiting mTOR activity (41, 47, 48).

Figure 19:
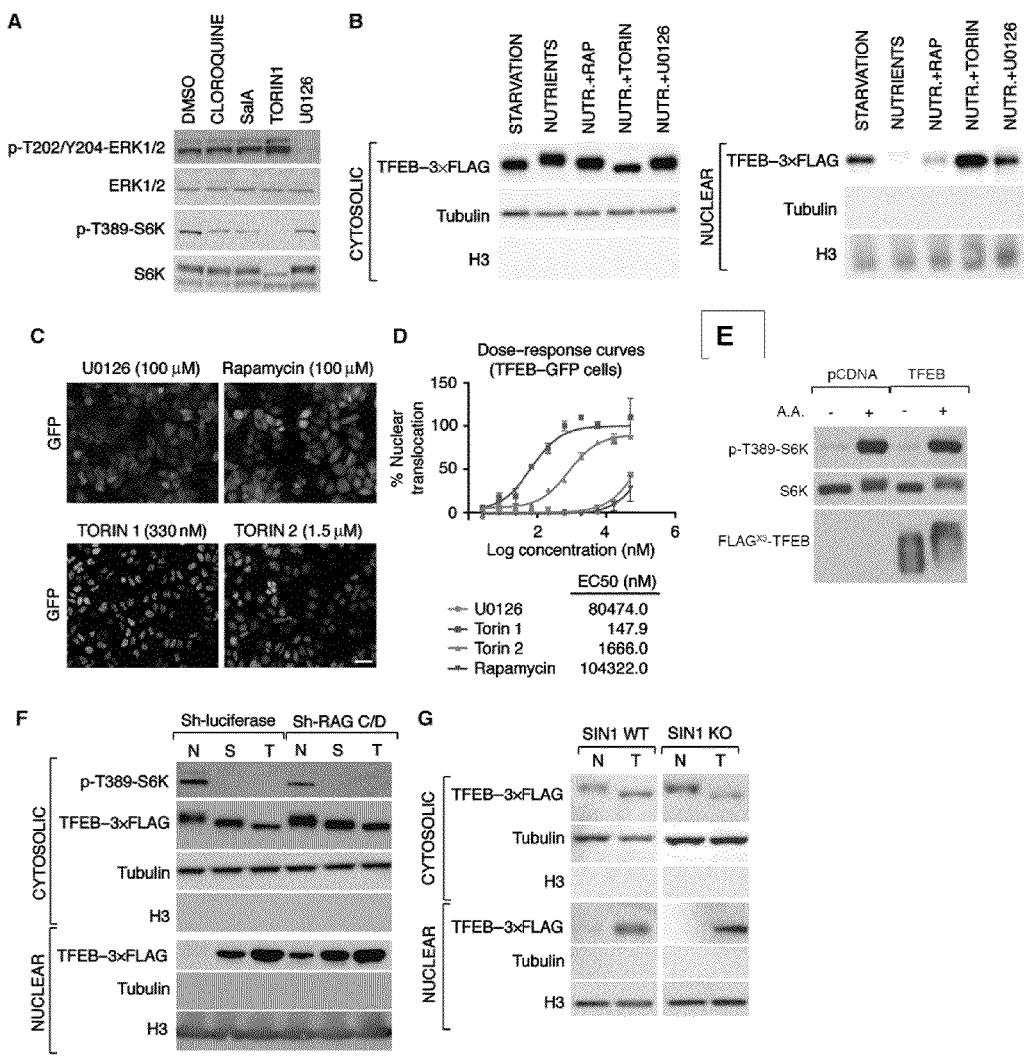
FIG. 19 mTORC1 regulates TFEB. (A) Lysosomal stress inhibits mTOR signalling. Immunoblotting of protein extracts isolated from HeLa cells treated overnight, as indicated. Membranes were probed with antibodies for p-T202/Y204-ERK1/2, ERK1/2, p-T389-S6K, and S6K to measure ERK and mTORC1 activities. (B) Torin 1 induces TFEB dephosphorylation and nuclear translocation. FLAG immunoblotting of cytosolic and nuclear fractions isolated from TFEB-3×FLAG HeLa cells cultured in amino acid-free media and subsequently stimulated as indicated for at least 3 h. Correct subcellular fractionation was verified with H3 and tubulin antibodies. (C, D) Effects and dose-response curves of ERK and mTOR inhibitors on TFEB nuclear translocation. TFEB-GFP HeLa cells were seeded in 384-well plates, incubated for 12 h, and treated with 10 different concentrations of the ERK inhibitor U0126 or the mTOR inhibitors Rapamycin, Torin 1 and Torin 2 ranging from 2.54 nM to 50 µM. After 3 h at 37° C. in RPMI medium containing one of each of the compounds, the cells were washed, fixed, and stained with DAPI and photographed by using confocal automated microscopy (Opera high content system, Perkin Elmer). (C) Representative images of test concentrations for each compound. Scale bars represent 30 µm. (D) The graph shows the percentage of nuclear translocation at the 10 different concentrations of each compound (in log of the concentration). The EC50 for each compound was calculated using Prism software (see Materials and Methods for details). (E) Amino acids induce TFEB molecular weight shift. Immunoblotting of protein extracts isolated from HEK-293T cells transfected either TFEB-3×FLAG or with an empty vector were nutrient starved and stimulated for 50 min with amino acids (a.a.). Antibody used were p-T389-S6K, S6K and FLAG. (F) Rag knockdown induces TFEB nuclear translocation. HeLa cells stably expressing Flag-3×TFEB were infected with lentiviruses encoding a Short hairpin (Sh-) RNA targeting luciferase (control) or RagC and RagD mRNAs. In all, 96 h post infection, cells were left untreated (N=normal media), starved (S=starved media) or treated with Torin 1 (T=Torin 1) for 4 h and then subjected to nuclear/cytosolic fractionation. TFEB localization was detected with a FLAG antibody, whereas tubulin and H3 were used as controls for the cytosolic and nuclear fraction, respectively; levels of S6K phosphorylation were used to test RagC and RagD knockdown efficiency. (G) mTORC2 does not affect TFEB phosphorylation. Mouse embryonic fibroblasts (MEFs) isolated from Sin1−/− or control embryos (E14.5) were infected with a retrovirus encoding TFEB-3×FLAG; 48 h post infection, cells were treated with Torin 1 (T) for 4 h, where indicated, subjected to nuclear/cytosolic fractionation and immunoblotted for FLAG, tubulin, and H3.

Applicants stimulated starved cells, in which TFEB is dephosphorylated and localized to the nucleus, with an amino-acid rich medium supplemented with Torin 1 (250 nM), Rapamycin (2.5 μM), or ERK inhibitor U0126 (50 μM). Stimulation of starved cells with nutrients alone induced a significant TFEB molecular weight shift and re-localization to the cytoplasm (FIG. 19B). Nutrient stimulation in the presence of the ERK inhibitor U0126 at a concentration of 50 μM induced only a partial TFEB molecular weight shift, suggesting that phosphorylation by ERK partially contributes to TFEB cytoplasmic localization. Treatment with 2.5 μM Rapamycin also resulted in a partial molecular weight shift but did not affect TFEB subcellular localization (FIG. 19B). However, Torin 1 (250 nM) treatment entirely prevented the molecular weight shift induced by nutrients and, in turn, resulted in massive TFEB nuclear accumulation. These data were confirmed in a cell-based high content assay using stable HeLa cells overexpressing TFEB fused to the green fluorescent protein (TFEB-GFP). In the assay imaging of treated cells is acquired by an automated confocal microscope (OPERA system) and the analysis of those images with Acapella image software calculates the ratio of the average of fluorescence intensity of TFEB-GFP between the cytosol and nucleus of the cell (see Materials and methods for details) (FIGS. 19 C and D). As Torin 1 inhibits both mTORC1 and mTORC2 complexes, applicants next evaluated the contribution of each complex to TFEB regulation. Three main observations suggest that TFEB is predominantly regulated by mTORC1: (1) stimulation of starved cells with amino acids, which activate mTORC1 but not mTORC2, induced an extensive TFEB molecular weight shift, which is highly suggestive of a phosphorylation event (FIG. 19E); (2) knockdown of RagC and RagD, which mediate amino-acid signals to mTORC1, caused TFEB nuclear accumulation even in cells kept in full nutrient medium (FIG. 19F); (3) in cells with disrupted mTORC2 signalling (Sin 1−/− mouse embryonic fibroblasts (MEFs)) (49, 50, 46) TFEB underwent a molecular weight shift and nuclear translocation upon Torin 1 treatment that were similar to control cells (FIG. 19G).

mTORC1 Controls TFEB Subcellular Localization Via the Phosphorylation of S142

To test whether mTORC1 phosphorylates TFEB at S142, applicants generated a phosphospecific antibody that recognizes TFEB only when phosphorylated at S142. Using this antibody, applicantsauthors observed that TFEB was no longer phosphorylated at S142 in HeLa cells stably overexpressing TFEB-3×FLAG and cultured in nutrient-depleted media, consistent with applicants' authors' results above reported (FIG. 20A).

Subsequently, they analysed the levels of S142 phosphoryation in starved cells supplemented with normal media with or without either Torin 1 or Rapamycin. While Torin 1 clearly blunted nutrient-induced S142 phosphorylation, rapamycin did not, suggesting that S142 represents a rapamycin-resistant mTORC1 site (FIG. 20A). These results clearly demonstrate that TFEB is an mTOR substrate and that S142 is a key residue for the phosphorylation of TFEB also by mTOR.

Figure 20:
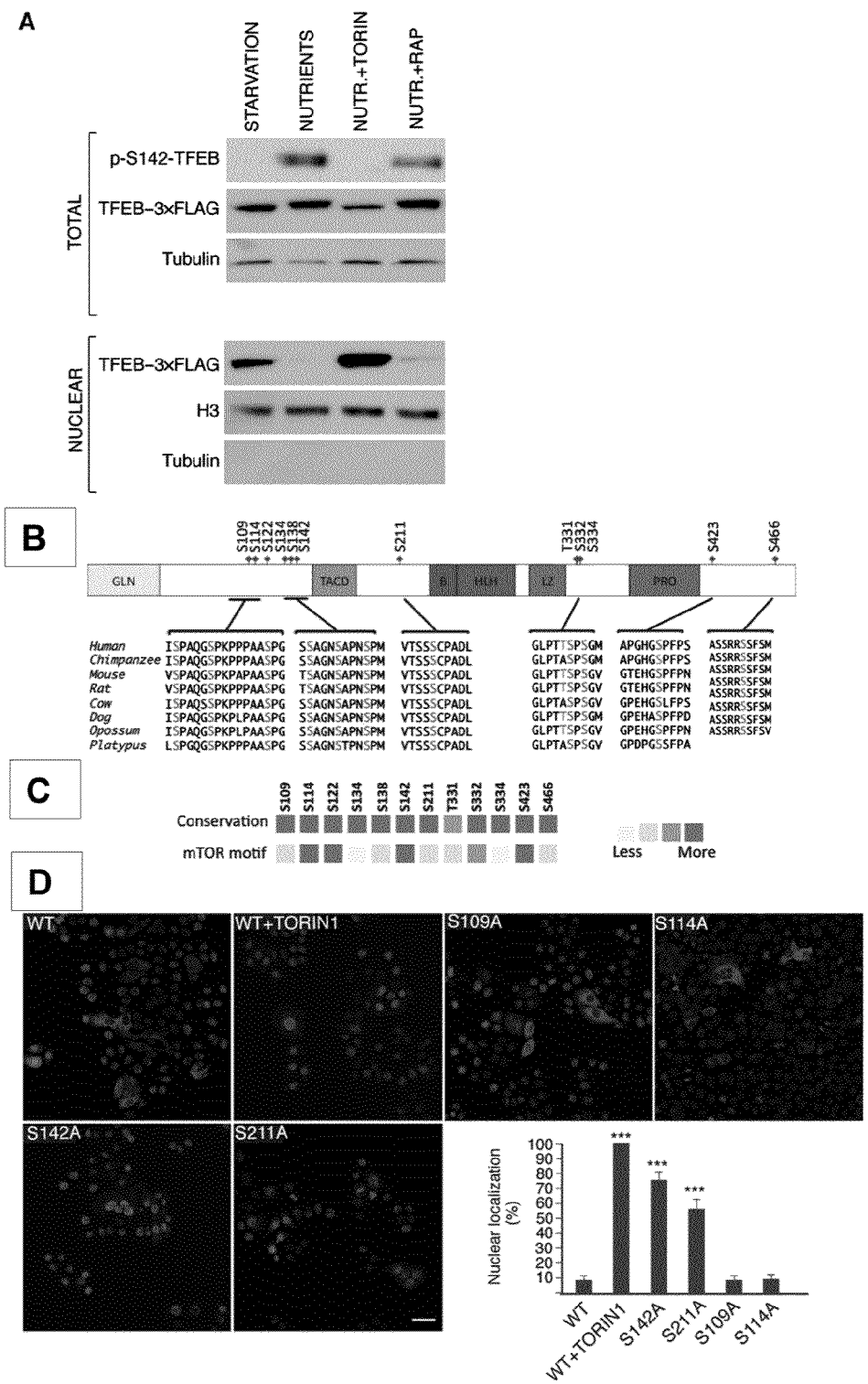
FIG. 20 mTORC1 phosphorylates TFEB at serine 142 (S142). (A) Torin 1 induces S142 dephosphorylation. HeLa cells were treated as indicated and total and nuclear extracts were probed with a TFEB p-S 142 phospho-antibody and with anti-FLAG antibody. (B) Schematic representation of TFEB protein structure with the predicted mTORC1 phosphorylation sites and their conservation among vertebrates. Numbering is according to human isoform 1. (C) Sequence conservation scores of the phosphorylation sites and quantitative agreement between mTOR consensus motif and the sequence around the phosphorylation sites of TFEB. (D) S142 and S211 regulate TFEB localization. Flag immunostaining of TFEB subcellular localization in HeLa cells expressing serine-to-alanine mutated versions of TFEB-3× Flag. Nuclei were stained with DAPI. Values are means of five fields containing at least 50 transfected cells. Student's t-test (unpaired) ***$P<0.001$. Scale bars represent 30 p.m.

Recent findings suggest that mTORC1 phosphorylates its target proteins at multiple sites (42, 43, 44). To identify additional serine residues that may be phosphorylated by mTOR, applicants searched for consensus phosphoacceptor motif for mTORC1 (42) in the coding sequence of TFEB (FIGS. 20 B and C). They mutagenized all TFEB amino-acid residues that were putative mTORC1 targets into alanines. Then they tested the effects of each of these mutations on TFEB subcellular localization and found that, similarly to S142A, a serine-to-alanine mutation at position 211 (S211A) resulted in a constitutive nuclear localization of TFEB (FIG. 20 D). Mutations of the other serine residues behaved similarly to the wild-type TFEB (FIG. 20D).

Together, these data indicate that, other than S 142, S211 also plays a role in TFEB subcellular localization and suggest that S211 represents an additional target site of mTORC1.

The Lysosome Regulates Gene Expression in TFEB

Figure 21:
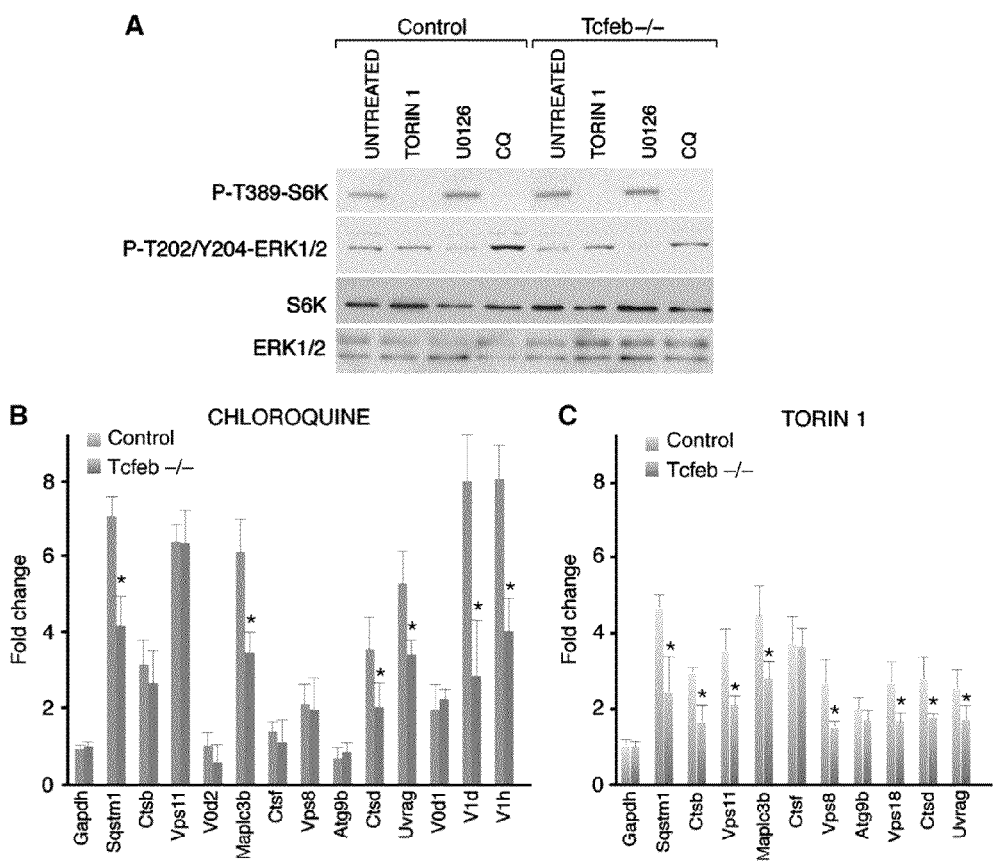
FIG. 21 The lysosome regulates gene expression by TFEB. (A) Chloroquine treatment inhibits mTORC1 activity in primary hepatocytes. Primary hepatocytes isolated from 2-month-old Tcfebflox/flox (control) and Tcfebflox/flox; Alb-Cre(Tcfeb−/−) mice were left untreated or treated overnight with Torin 1, U0126, or Chloroquine. Subsequently, cells were lysed and protein extracts were immunoblotted with the indicated antibodies. (B, C) TFEB mediates the transcriptional response to chloroquine and Torin 1. Quantitative PCR (qPCR) of TFEB target genes in primary hepatocytes from control (flox/flox) and Tcfeb−/− (flox/flox; alb-Cre) mice. Cells were treated with Chloroquine (left) and Torin 1 (right). The expression levels are shown as % increased expression of the treated versus the corresponding untreated samples. Values represent means±s.d. of three inde-

As the interaction of TFEB with mTORC1 controls TFEB nuclear translocation, applicants tested whether the ability of TFEB to regulate gene expression was also influenced by this interaction. The expression of several lysosomal/autophagic genes that were shown to be targets of TFEB (37) was tested in primary hepatocytes from a conditional knockout mouse line in which TFEB was deleted in the liver (Tcfeb$^{flox/flox}$; alb-CRE), and in a control mouse line (Tcfeb$^{flox/flox}$). Cells were treated with either chloroquine or Torin 1, or left untreated. These treatments inhibited mTOR as measured by the level of p-S6K, whereas the levels of p-ERK were unaffected (FIG. 21A). Primary hepatocytes isolated from TFEB conditional knockout mice cultured in regular medium did not show significant differences in the expression levels of several TFEB target genes compared with control hepatocytes. However, while the expression of TFEB target genes was upregulated in hepatocytes from control mice after treatment with chloroquine, this upregulation was significantly blunted in hepatocytes from TFEB conditional knockout mice (FIG. 21B). Similarly, the transcriptional response upon Torin 1 treatment was significantly reduced in hepatocytes from TFEB conditional knockout mice (FIG. 21C). Together, these results indicate that TFEB plays a key role in the transcriptional response induced by the lysosome via mTOR.

Both transcriptional-dependent (24, 25) and independent mechanisms regulating autophagy have been described (26, 27). The study identifies novel, kinase-dependent, regulatory circuits that control multiple crucial steps of the autophagic pathway such as autophagosome formation, autophagosome-lysosome fusion and lysosome-mediated degradation of the autophagosomal content. Interestingly, applicants observed that the transcriptional induction of the autophagic/lysosomal genes precedes autophagosome formation. It could be envisaged that such transcriptional-dependent mechanism ensures a more prolonged and sustained activation of autophagy.

Autophagy dysfunction has been linked to several genetic disorders (28-30)), by contrary previous studies showed that enhancement of autophagy has a therapeutic effect in animal models of neurodegenerative diseases and hepatic fibrosis (29, 31, 32).

Figure 16:
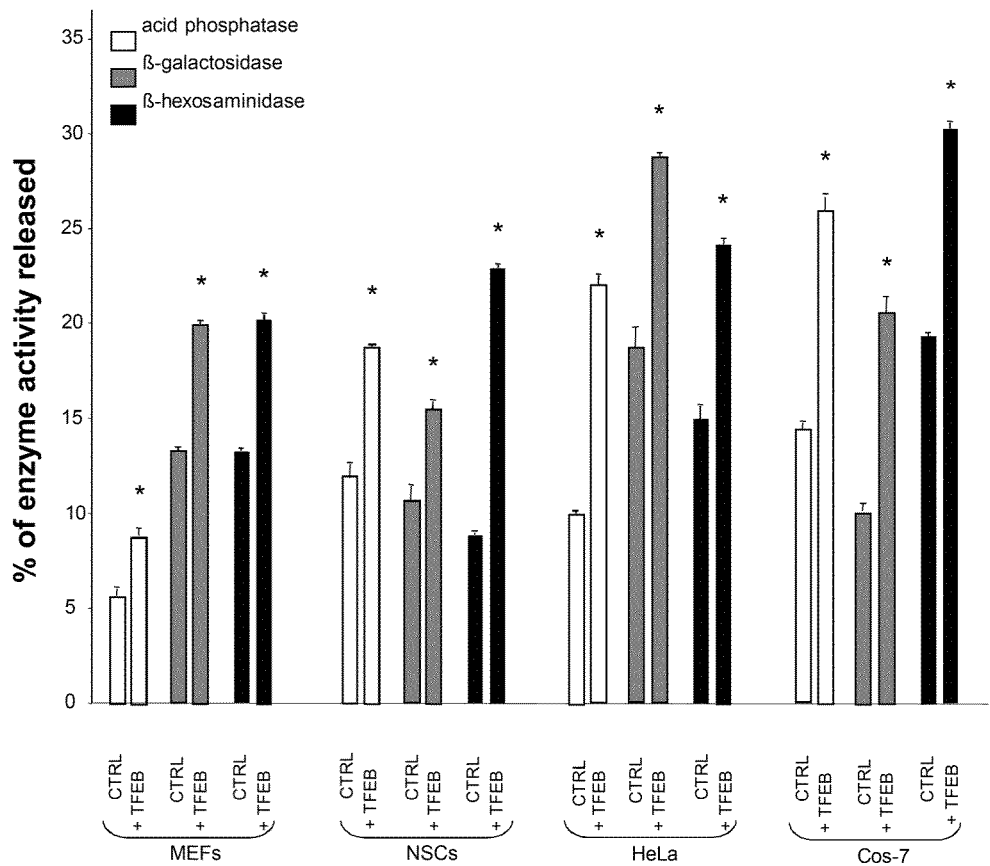
FIG. 16 TFEB overexpression increases the release of lysosomal enzymes in the culture medium of MEFs, NSCs, HeLa, and COS-7 cells. Activities of lysosomal enzymes acid phosphatase, beta-galactosidase, and beta-hexosaminidase were determined in the culture medium and in cells transfected with either an empty vector or with a TFEB-expression vector. HeLa, Cos7 cells and mouse embryonic fibroblasts from mouse models of MLIV (S7), MPSIIIA (S7), and MSD were transfected using PolyFect Transfection Reagent (Qiagen) or lipofectamine 2000 Reagent (Invitrogen), according to the manufacturer's protocols. TFEB-3×FLAG HeLa stable cell lines (CF7) was previously described (2). The figure shows percentages of enzyme activities released compared to total activities.
Figure 17:
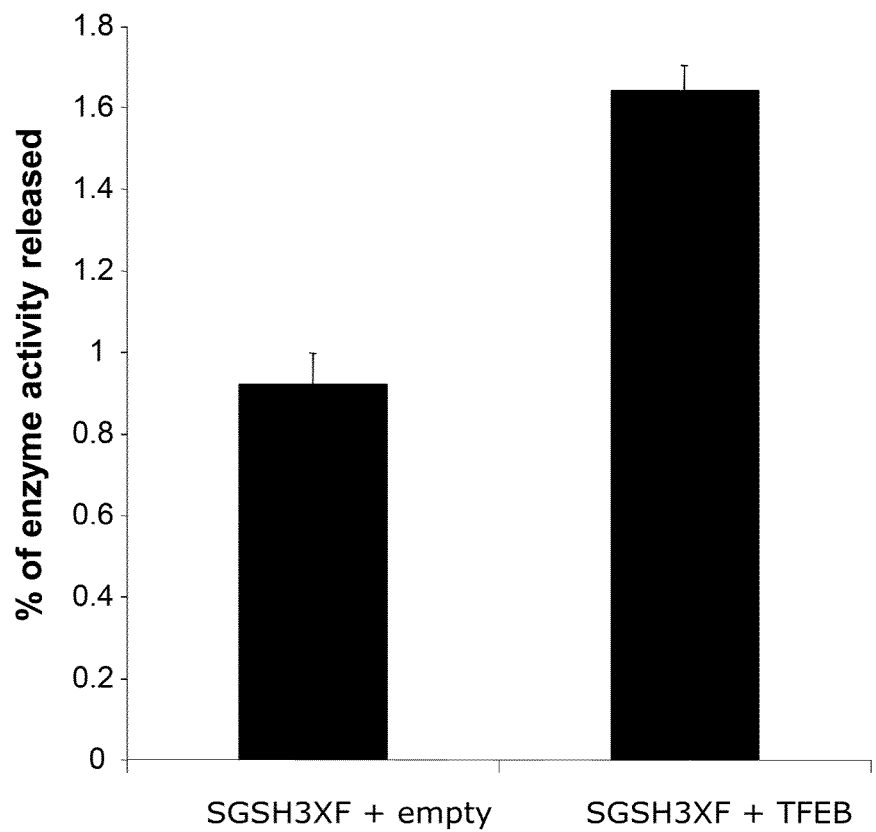
FIG. 17 TFEB exerts a positive control on lysosomal exocytosis. MPSIIIA MEF Cells were maintained in DMEM supplemented with 10% FBS and penicillin/streptomycin (normal culture medium). Sub-confluent cells were transfected using Lipofectamine™ 2000 (Invitrogen) according to manufacturer's protocols. MPS-IIIA MEFs were co-transfected with a plasmid encoding a tagged sulfamidase (SGSH3×Flag) and either an empty plasmid or a plasmid encoding TFEB. One day after transfection the medium was replaced with DMEM 0.5% FBS. Two days after transfection the conditioned medium and the pellet were collected for sulfamidase activity measurement and the percentage of the enzyme released in the medium calculated.

The discovery of a novel mechanism that controls, at the transcriptional level, the lysosomal-autophagic pathway suggests novel approaches to modulate cellular clearance in these diseases. Furthermore, it provides a spin-off for therapeutic approaches based on lysosomal enzymes, suggesting new strategies for increasing the productivity of cell lines producing endogenous or recombinant lysosomal enzymes (FIGS. 16 and 17). Moreover, TFEB overexpression was able to promote substrate clearance and to rescue cellular vacuolization in LSDs (45); thus, the identification of a phosphorylation-mediated mechanism that regulates TFEB activity offers a new tool to promote cellular clearance in health and disease.

TABLE 1

Gene expression changes in response to TFEB overexpression or cell starvation5(Pearson Correlation 0.42)

| GENE SYMBOL | TFEB stable OVEREXPRESSION FOLD INCREASE | GENE SYMBOL | CELL STARVATION FOLD INCREASE |
|---|---|---|---|
| AKT1 | 1.2 | AKT1 | 1.1 |
| AMBRA1 | 1.2 | AMBRA1 | 1.3 |
| APP | 1.4 | APP | 1.2 |
| ARSA | 1.3 | ARSA | 1.4 |
| ATG10 | 1.1 | ATG10 | 1.0 |
| ATG12 | 1.2 | ATG12 | 1.2 |
| ATG16L1 | −1.2 | ATG16L1 | −1.5 |
| ATG16L2 | 1.1 | ATG16L2 | 1.0 |
| ATG3 | 1.2 | ATG3 | 1.0 |
| ATG4A | 1.2 | ATG4A | −1.2 |
| ATG4B | 1.3 | ATG4B | 1.1 |
| ATG4C | 1.1 | ATG4C | 1.1 |
| ATG4D | 1.6 | ATG4D | 1.8 |
| ATG5 | 1.2 | ATG5 | 1.1 |
| ATG7 | 1.2 | ATG7 | 1.0 |
| ATG9A | 1.1 | ATG9A | 1.3 |
| ATG9B | 5.6 | ATG9B | 1.8 |
| BAD | 1.0 | BAD | 1.0 |
| BAK1 | 1.4 | BAK1 | 1.0 |
| BAX | 1.2 | BAX | 1.1 |
| BCL2 | 1.5 | BCL2 | 1.4 |
| BECN1 | 1.2 | BECN1 | 1.0 |
| BID | 1.2 | BID | 1.1 |
| BNIP3 | 1.1 | BNIP3 | 1.1 |
| CLN3 | 1.5 | CLN3 | 1.2 |
| CXCR4 | 1.3 | CXCR4 | 1.2 |
| DRAM | 1.8 | DRAM | −1.3 |
| EIF2AK3 | 1.4 | EIF2AK3 | 1.2 |
| EIF4G1 | 1.3 | EIF4G1 | −1.2 |
| FAM176A | 1.6 | FAM176A | −1.3 |
| GAA | 1.3 | GAA | 1.2 |
| GABARAP | 1.1 | GABARAP | 1.3 |
| GABARAPL1 | 1.0 | GABARAPL1 | 1.2 |
| GABARAPL2 | 1.1 | GABARAPL2 | 1.0 |
| HGS | −1.1 | HGS | −1.2 |
| HTT | 1.0 | HTT | 1.0 |
| MAP1LC3A | 1.1 | MAP1LC3A | 1.4 |
| MAP1LC3B | 1.2 | MAP1LC3B | 1.2 |
| PIK3C3 | −1.2 | PIK3C3 | −1.2 |
| PIK3R4 | 1.1 | PIK3R4 | −1.2 |
| PTEN | 1.1 | PTEN | 1.1 |
| RAB24 | 1.2 | RAB24 | 1.2 |
| RGS19 | 1.2 | RGS19 | −1.2 |
| SNCA | 1.6 | SNCA | −1.2 |
| SQSTM1 | 2.4 | SQSTM1 | 1.6 |
| TP53 | 1.1 | TP53 | 1.0 |
| ULK1 | 1.1 | ULK1 | 2.0 |
| UVRAG | 1.8 | UVRAG | 2.4 |
| VPS11 | 1.4 | VPS11 | 1.6 |
| VPS18 | 1.4 | VPS18 | 1.4 |
| WIPI | 2.5 | WIPI | 1.5 |

Pearson product-moment correlation coefficient (PMCC) was obtained by comparing the gene expression profiles shown, i.e. TFEB stable overexpression vs. gene expression profiles of starved HeLa cells.

TABLE 2

Gene expression changes in response to TFEB inhibition using siRNA

| GENE SYMBOL | FOLD INCREASE |
|---|---|
| AKT1 | −2.1962 |
| AMBRA1 | 1.1134 |
| APP | −1.1769 |
| ARSA | −2.858 |
| ATG10 | 1.0389 |
| ATG12 | 1.0461 |
| ATG16L1 | −1.6529 |
| ATG16L2 | −1.3333 |
| ATG3 | 1.2702 |
| ATG4A | −1.3333 |
| ATG4B | −1.244 |
| ATG4C | −1.6077 |
| ATG4D | −1.1527 |
| ATG5 | −1.0607 |
| ATG7 | −1.6994 |
| ATG9A | −1.9793 |
| ATG9B | −4.4229 |
| BAK1 | 1.4489 |
| BAX | −1.3803 |
| BCL2 | −2.3054 |
| BECN1 | −1.1769 |
| BID | 1.3241 |
| BNIP3 | −1.1212 |
| CLN3 | −1.4692 |
| CXCR4 | −1.5529 |
| DRAM | −1.1769 |
| EIF2AK3 | −1.3996 |
| EIF4G1 | −2.3702 |
| ESR1 | −1.676 |
| GAA | −1.3613 |
| GABARAP | 1.4093 |
| GABARAPL1 | −1.2016 |
| GABARAPL2 | 1.3899 |
| HGS | −1.5594 |
| HTT | −1.3899 |
| MAP1LC3A | −1.0389 |
| MAP1LC3B | −1.4175 |
| PIK3R4 | −1.6189 |
| PTEN | −1.2702 |
| RAB24 | 1.3333 |
| SNCA | 1.2269 |
| SQSTM1 | −1.4093 |
| TP53 | −1.279 |
| ULK1 | −3.668 |
| UVRAG | −1.3059 |
| VPS11 | −1.84 |
| VPS18 | −2.1 |
| WIPI | −1.94 |

Down-regulated genes upon siRNA-mediated TFEB knock-down. Fold change represents the average of 4 independent experiments. Genes significantly down-regulated are indicated in red ($p < 0.05$).

TABLE 4

Prediction of S142 phosphorylation using different methods

| METHODS | Cutoff | Actual prediction for S142 | Group | Family | Subfamily | Kinase |
|---|---|---|---|---|---|---|
| CrPhos0.8 | FPR ≤ 30% | MAPK8 | CMGC | MAPK | JNK | MAPK8 |
| CrPhos0.8 | FPR ≤ 30% | MAPK3 | CMGC | MAPK | ERK | MAPK3 |
| CrPhos0.8 | FPR ≤ 30% | MAPK1 | CMGC | MAPK | ERK | MAPK1 |
| CrPhos0.8 | FPR ≤ 30% | CDK2 | CMGC | CDK | CDK2 | CDK2 |
| GPS-2.1 | Score ≥ 5 | CMGC/CDK/CDK5 | CMGC | CDK | CDK5 | |
| GPS-2.1 | Score ≥ 5 | CMGC/CDK/CDK4/CDK4 | CMGC | CDK | CDK4 | CDK4 |
| GPS-2.1 | Score ≥ 5 | CMGC/MAPK/ERK/MAPK1 | CMGC | MAPK | ERK | MAPK1 |
| GPS-2.1 | Score ≥ 5 | CMGC/MAPK/ERK/MAPK3 | CMGC | MAPK | ERK | MAPK3 |
| GPS-2.1 | Score ≥ 5 | CMGC/MAPK/JNK/MAPK8 | CMGC | MAPK | JNK | MAPK8 |
| GPS-2.1 | Score ≥ 5 | CMGC/MAPK/JNK/MAPK10 | CMGC | MAPK | JNK | MAPK10 |
| GPS-2.1 | Score ≥ 5 | STE/STE7/MAP2K7 | STE | STE7 | MAP2K7 | |
| GPS-2.1 | Score ≥ 5 | CMGC/MAPK/p38/MAPK12 | CMGC | MAPK | p38 | MAPK12 |
| PhosphoMotifFinder | | GSK3 | CMGC | GSK | GSK3 | |
| PhosphoMotifFinder | | ERK1 | CMGC | MAPK | ERK | MAPK3 |
| PhosphoMotifFinder | | ERK2 | CMGC | MAPK | ERK | MAPK1 |
| PhosphoMotifFinder | | ERK3 | CMGC | MAPK | ERK | MAPK6 |
| PhosphoMotifFinder | | CDK5 | CMGC | CDK | CDK5 | CDK5 |
| Networkin | | p38MAPK/MAPK9 | CMGC | MAPK | JNK | MAPK9 |
| Networkin | | GSK3/GSK3B | CMGC | GSK | GSK3 | GSK3B |
| Networkin | | CDK5/CDK2 | CMGC | CDK | CDK2 | CDK2 |
| networkin 2 | | CDK2_CDK3/CDK2 | CMGC | CDK | CDK2 | CDK2 |
| PHOSIDA | | CK1_group | CK1 | CK1 | | |
| PHOSIDA | | ERK | CMGC | MAPK | ERK | |

Results of the prediction of phosphorylation of S142 using five different methods. Methods are given in the first column. The second column indicates confidence score cutoff as described in methods, when available. The third column shows the actual format of prediction obtained by the corresponding method. The next four columns show the prediction in the kinase group, kinase family, kinase subfamily and kinase protein classifications, respectively.

REFERENCES

1 He, C. & Klionsky, D. J. Regulation mechanisms and signaling pathways of autophagy. *Annu Rev Genet* 43, 67-93 (2009).
2 Sardiello, M. et al. A gene network regulating lysosomal biogenesis and function. *Science* 325, 473-477 (2009).
3 Lum, J. J. et al. Growth factor regulation of autophagy and cell survival in the absence of apoptosis. *Cell* 120, 237-248 (2005).
4 Klionsky, D. J., Elazar, Z., Seglen, P. O. & Rubinsztein, D. C. Does bafilomycin A1 block the fusion of autophagosomes with lysosomes? Autophagy 4, 849-950 (2008).
5 Xie, Z. & Klionsky, D. J. Autophagosome formation: core machinery and adaptations. *Nat Cell Biol* 9, 1102-1109 (2007).
6 Rubinsztein, D. C. et al. In search of an "autophagomometer". *Autophagy* 5, 585-589 (2009).
7 Mizushima, N., Yoshimori, T. & Levine, B. Methods in mammalian autophagy research. *Cell* 140, 313-326 (2010).
8 Klionsky, D. J., Cuervo, A. M. & Seglen, P. O. Methods for monitoring autophagy from yeast to human. *Autophagy* 3, 181-206 (2007).
9 Kimura, S., Noda, T. & Yoshimori, T. Dissection of the autophagosome maturation process by a novel reporter protein, tandem fluorescent-tagged LC3. *Autophagy* 3, 452-460 (2007).
10 Bauvy, C., Meijer, A. J. & Codogno, P. Assaying of autophagic protein degradation. *Methods Enzymol* 452, 47-61 (2009).
11 Mizushima, N., Yamamoto, A., Matsui, M., Yoshimori, T. & Ohsumi, Y. In vivo analysis of autophagy in response to nutrient starvation using transgenic mice expressing a fluorescent autophagosome marker. *Mol Biol Cell* 15, 1101-1111 (2004).
12 Mizushima, N. Autophagy: process and function. *Genes Dev* 21, 2861-2873 (2007).
13 Behrends, C., Sowa, M. E., Gygi, S. P. & Harper, J. W. Network organization of the human autophagy system. *Nature* 466, 68-76 (2010).
14 Liang, C. et al. Beclin1-binding UVRAG targets the class C Vps complex to coordinate autophagosome maturation and endocytic trafficking. *Nat Cell Biol* 10, 776-787 (2008).
15 Dang, T. H., Van Leemput, K., Verschoren, A. & Laukens, K. Prediction of kinase-specific phosphorylation sites using conditional random fields. *Bioinformatics* 24, 2857-2864 (2008).
16 Xue, Y. et al. GPS 2.0, a tool to predict kinase-specific phosphorylation sites in hierarchy. *Mol Cell Proteomics* 7, 1598-1608 (2008).
17 Amanchy, R. et al. A curated compendium of phosphorylation motifs. *Nat Biotechnol* 25, 285-286 (2007).
18 Linding, R. et al. Systematic discovery of in vivo phosphorylation networks. *Cell* 129, 1415-1426 (2007).
19 Gnad, F. et al. PHOSIDA (phosphorylation site database): management, structural and evolutionary investigation, and prediction of phosphosites. *Genome Biol* 8, R250 (2007).
20 Hemesath, T. J., Price, E. R., Takemoto, C., Badalian, T. & Fisher, D. E. MAP kinase links the transcription factor Microphthalmia to c-Kit signalling in melanocytes. *Nature* 391, 298-301 (1998).
21 Kolch, W. Coordinating ERK/MAPK signalling through scaffolds and inhibitors. *Nat Rev Mol Cell Biol* 6, 827-837 (2005).
22 Corcelle, E. et al. Disruption of autophagy at the maturation step by the carcinogen lindane is associated with the sustained mitogen-activated protein kinase/extracellular signal-regulated kinase activity. *Cancer Res* 66, 6861-6870 (2006).

23 Lipinski, M. M. et al. A genome-wide siRNA screen reveals multiple mTORC1 independent signaling pathways regulating autophagy under normal nutritional conditions. *Dev Cell* 18, 1041-1052 (2010).

24 Zhao, J. et al. FoxO3 coordinately activates protein degradation by the autophagic/lysosomal and proteasomal pathways in atrophying muscle cells. *Cell Metab* 6, 472-483 (2007).

25 Mammucari, C. et al. FoxO3 controls autophagy in skeletal muscle in vivo. *Cell Metab* 6, 458-471 (2007).

26 He, C. & Levine, B. The Beclin 1 interactome. *Curr Opin Cell Biol* 22, 140-149 (2010).

27 Neufeld, T. P. TOR-dependent control of autophagy: biting the hand that feeds. *Curr Opin Cell Biol* 22, 157-168 (2010).

28 Wong, E. & Cuervo, A. M. Autophagy gone awry in neurodegenerative diseases. *Nat Neurosci* 13, 805-811 (2010).

29 Levine, B. & Kroemer, G. Autophagy in the pathogenesis of disease. *Cell* 132, 27-42 (2008).

30 Settembre, C. et al. A block of autophagy in lysosomal storage disorders. *Hum Mol Genet* 17, 119-129 (2008).

31 Hidvegi, T. et al. An autophagy-enhancing drug promotes degradation of mutant alpha1-antitrypsin Z and reduces hepatic fibrosis. *Science* 329, 229-232 (2010).

32 Rubinsztein, D. C., Gestwicki, J. E., Murphy, L. O. & Klionsky, D. J. Potential therapeutic applications of autophagy. *Nat Rev Drug Discov* 6, 304-312 (2007).

33 Fraldi, A., Hemsley, K., Crawley, A., Lombardi, A., Lau, A., Sutherland, L., Auricchio, A., Ballabio, A. and Hopwood, J. J. Functional correction of CNS lesions in an MPS-IIIA mouse model by intracerebral AAV-mediated delivery of sulfamidase and SUMF1 genes. *Hum Mol Genet,* 16, 2693-702 (2007).

34 Ballabio A, Gieselmann V (2009) Lysosomal disorders: from storage to cellular damage. *Biochim Biophys Acta* 1793: 684-696

35 Luzio J P, Pryor P R, Bright N A (2007) Lysosomes: fusion and function. *Nat Rev Mol Cell Biol* 8: 622-632

36 Saftig P, Klumperman J (2009) Lysosome biogenesis and lysosomal membrane proteins: trafficking meets function. *Nat Rev Mol Cell Biol* 10: 623-635

37 Palmieri M, Impey S, Kang H, di Ronza A, Pelz C, Sardiello M, Ballabio A (2011) Characterization of the CLEAR network reveals an integrated control of cellular clearance pathways. *Hum Mol Genet* 20: 3852-3866

38 Xie X S, Padron D, Liao X, Wang J, Roth M G, De Brabander J K (2004) Salicylihalamide A inhibits the V0 sector of the V-ATPase through a mechanism distinct from bafilomycin A1. J Biol Chem 279: 19755-19763

39 Sancak Y, Bar-Peled L, Zoncu R, Markhard A L, Nada S, Sabatini D M (2010) Ragulator-Rag complex targets mTORC1 to the lysosomal surface and is necessary for its activation by amino acids. Cell 141: 290-303

40 Zoncu R, Bar-Peled L, Efeyan A, Wang S, Sancak Y, Sabatini D M (2011a) mTORC1 senses lysosomal amino acids through an inside-out mechanism that requires the vacuolar H-ATPase. *Science* 334: 678-683

41 Thoreen C C, Kang S A, Chang J W, Liu Q, Zhang J, Gao Y, Reichling L J, Sim T, Sabatini D M, Gray N S (2009) An ATP-competitive mammalian target of rapamycin inhibitor reveals rapamycin-resistant functions of mTORC1. *J Biol Chem* 284: 8023-8032

42 Hsu P P, Kang S A, Rameseder J, Zhang Y, Ottina K A, Lim D, Peterson T R, Choi Y, Gray N S, Yaffe M B, Marto J A, Sabatini D M (2011) The mTOR-regulated phosphoproteome reveals a mechanism of mTORC1-mediated inhibition of growth factor signaling. Science 332: 1317-1322

43 Peterson T R, Sengupta S S, Harris T E, Carmack A E, Kang S A, Balderas E, Guertin D A, Madden K L, Carpenter A E, Finck B N, Sabatini D M (2011) mTOR complex 1 regulates lipin 1 localization to control the SREBP pathway. Cell 146: 408-420

44 Yu Y, Yoon S O, Poulogiannis G, Yang Q, Ma X M, Villen J, Kubica N, Hoffman G R, Cantley L C, Gygi S P, Blenis J (2011) Phosphoproteomic analysis identifies Grb10 as an mTORC1 substrate that negatively regulates insulin signaling. Science 332: 1322-1326

45 Medina D L, Fraldi A, Bouche V, Annunziata F, Mansueto G, Spampanato C, Puri C, Pignata A, Martina J A, Sardiello M, Palmieri M, Polishchuk R, Puertollano R, Ballabio A (2011) Transcriptional activation of lysosomal exocytosis promotes cellular clearance. *Dev Cell* 21: 421-430

46 Jacinto E, Facchinetti V, Liu D, Soto N, Wei S, Jung S Y, Huang Q, Qin J, Su B (2006) SIN1/MIP1 maintains rictor-mTOR complex integrity and regulates Akt phosphorylation and substrate specificity. Cell 127: 125-137

47 Feldman M E, Apsel B, Uotila A, Loewith R, Knight Z A, Ruggero D, Shokat K M (2009) Active-site inhibitors of mTOR target rapamycin-resistant outputs of mTORC1 and mTORC2. *PLoS Biol* 7: e38

48 Garcia-Martinez J M, Moran J, Clarke R G, Gray A, Cosulich S C, Chresta C M, Alessi D R (2009) Ku-0063794 is a specific inhibitor of the mammalian target of rapamycin (mTOR). *Biochem J* 421: 29-42

49 Frias M A, Thoreen C C, Jaffe J D, Schroder W, Sculley T, Can S A, Sabatini D M (2006) mSin1 is necessary for Akt/PKB phosphorylation, and its isoforms define three distinct mTORC2s. *Curr Biol* 16: 1865-1870

50 Yang Q, Inoki K, Ikenoue T, Guan K L (2006) Identification of Sin 1 as an essential TORC2 component required for complex formation and kinase activity. *Genes & development* 20: 2820-2832

The invention claimed is:

1. A transcription factor EB (TFEB) variant protein,
   (a) wherein the TFEB variant protein comprises SEQ ID NO: 2, wherein Ser is replaced by a non-serine amino acid residue at positions 142 and/or 211 of SEQ ID NO: 2; or
   (b) wherein the TFEB variant protein consists of amino acid residues 117 to 166 of SEQ ID NO: 2, wherein Ser is replaced by a non-serine amino acid residue at a position corresponding to position 142 of SEQ ID NO: 2 wherein said variant protein induces autophagy.

2. The TFEB variant protein according to claim 1 wherein the non-serine amino acid residue is Ala.

3. The TFEB variant protein according to claim 1, part (a) consisting of SEQ ID NO: 2, wherein Ser is replaced by a non-serine amino acid residue at amino acid residue positions 142 and/or 211.

4. The TFEB variant protein according to claim 1, part (a).

5. The TFEB variant protein according to claim 1, part (b).

\* \* \* \* \*

SEQUENCE LISTING

```
<160> NUMBER OF SEQ ID NOS: 4

<210> SEQ ID NO 1
<211> LENGTH: 1431
<212> TYPE: DNA
<213> ORGANISM: Homo sapiens
<220> FEATURE:
<221> NAME/KEY: CDS
<222> LOCATION: (1)..(1431)

<400> SEQUENCE: 1
```

-continued

```
atg gcg tca cgc ata ggg ttg cgc atg cag ctc atg cgg gag cag gcg      48
Met Ala Ser Arg Ile Gly Leu Arg Met Gln Leu Met Arg Glu Gln Ala
1               5                   10                  15 cag cag gag gag cag cgg gag cgc atg cag caa cag gct gtc atg cat      96
Gln Gln Glu Glu Gln Arg Glu Arg Met Gln Gln Gln Ala Val Met His
            20                  25                  30 tac atg cag cag cag cag cag cag caa cag cag ctc gga ggg ccg         144
Tyr Met Gln Gln Gln Gln Gln Gln Gln Gln Gln Leu Gly Gly Pro
        35                  40                  45 ccc acc ccg gcc atc aat acc ccc gtc cac ttc cag tcg cca cca cct    192
Pro Thr Pro Ala Ile Asn Thr Pro Val His Phe Gln Ser Pro Pro Pro
50                  55                  60 gtg cct ggg gag gtg ttg aag gtg cag tcc tac ctg gag aat ccc aca    240
Val Pro Gly Glu Val Leu Lys Val Gln Ser Tyr Leu Glu Asn Pro Thr
65                  70                  75                  80 tcc tac cat ctg cag cag tcg cag cat cag aag gtg cgg gag tac ctg    288
Ser Tyr His Leu Gln Gln Ser Gln His Gln Lys Val Arg Glu Tyr Leu
            85                  90                  95 tcc gag acc tat ggg aac aag ttt gct gcc cac atc agc cca gcc cag    336
Ser Glu Thr Tyr Gly Asn Lys Phe Ala Ala His Ile Ser Pro Ala Gln
            100                 105                 110 ggc tct ccg aaa ccc cca cca gcc gcc tcc cca ggg gtg cga gct gga    384
Gly Ser Pro Lys Pro Pro Pro Ala Ala Ser Pro Gly Val Arg Ala Gly
        115                 120                 125 cac gtg ctg tcc tcc tcc gct ggc aac agt gct ccc aat agc ccc atg    432
His Val Leu Ser Ser Ser Ala Gly Asn Ser Ala Pro Asn Ser Pro Met
130                 135                 140 gcc atg ctg cac att ggc tcc aac cct gag agg gag ttg gat gat gtc    480
Ala Met Leu His Ile Gly Ser Asn Pro Glu Arg Glu Leu Asp Asp Val
145                 150                 155                 160 att gac aac att atg cgt ctg gac gat gtc ctt ggc tac atc aat cct    528
Ile Asp Asn Ile Met Arg Leu Asp Asp Val Leu Gly Tyr Ile Asn Pro
                165                 170                 175 gaa atg cag atg ccc aac acg cta ccc ctg tcc agc agc cac ctg aat    576
Glu Met Gln Met Pro Asn Thr Leu Pro Leu Ser Ser Ser His Leu Asn
            180                 185                 190 gtg tac agc agc gac ccc cag gtc aca gcc tcc ctg gtg ggc gtc acc    624
Val Tyr Ser Ser Asp Pro Gln Val Thr Ala Ser Leu Val Gly Val Thr
        195                 200                 205 agc agc tcc tgc cct gcg gac ctg acc cag aag cga gag ctc aca gat    672
Ser Ser Ser Cys Pro Ala Asp Leu Thr Gln Lys Arg Glu Leu Thr Asp
210                 215                 220 gct gag agc agg gcc ctg gcc aag gag cgg cag aag aaa gac aat cac    720
Ala Glu Ser Arg Ala Leu Ala Lys Glu Arg Gln Lys Lys Asp Asn His
225                 230                 235                 240 aac tta att gaa agg aga cga agg ttc aac atc aat gac cgc atc aag    768
Asn Leu Ile Glu Arg Arg Arg Arg Phe Asn Ile Asn Asp Arg Ile Lys
                245                 250                 255 gag ttg gga atg ctg atc ccc aag gcc aat gac ctg gac gtg cgc tgg    816
Glu Leu Gly Met Leu Ile Pro Lys Ala Asn Asp Leu Asp Val Arg Trp
            260                 265                 270 aac aag ggc acc atc ctc aag gcc tct gtg gat tac atc cgg agg atg    864
Asn Lys Gly Thr Ile Leu Lys Ala Ser Val Asp Tyr Ile Arg Arg Met
        275                 280                 285 cag aag gac ctg caa aag tcc agg gag ctg gag aac cac tct cgc cgc    912
Gln Lys Asp Leu Gln Lys Ser Arg Glu Leu Glu Asn His Ser Arg Arg
290                 295                 300 ctg gag atg acc aac aag cag ctc tgg ctc cgt atc cag gag ctg gag    960
Leu Glu Met Thr Asn Lys Gln Leu Trp Leu Arg Ile Gln Glu Leu Glu
305                 310                 315                 320
```

-continued

```
atg cag gct cga gtg cac ggc ctc cct acc acc tcc ccg tcc ggc atg    1008
Met Gln Ala Arg Val His Gly Leu Pro Thr Thr Ser Pro Ser Gly Met
            325                 330                 335 aac atg gct gag ctg gcc cag cag gtg gtg aag cag gag ctg cct agc    1056
Asn Met Ala Glu Leu Ala Gln Gln Val Val Lys Gln Glu Leu Pro Ser
        340                 345                 350 gaa gag ggc cca ggg gag gcc ctg atg ctg ggg gct gag gtc cct gac    1104
Glu Glu Gly Pro Gly Glu Ala Leu Met Leu Gly Ala Glu Val Pro Asp
    355                 360                 365 cct gag cca ctg cca gct ctg ccc ccg caa gcc ccg ctg ccc ctg ccc    1152
Pro Glu Pro Leu Pro Ala Leu Pro Pro Gln Ala Pro Leu Pro Leu Pro
370                 375                 380 acc cag cca cca tcc cca ttc cat cac ctg gac ttc agc cac agc ctg    1200
Thr Gln Pro Pro Ser Pro Phe His His Leu Asp Phe Ser His Ser Leu
385                 390                 395                 400 agc ttt ggg ggc agg gag gac gag ggt ccc ccg ggc tac ccc gaa ccc    1248
Ser Phe Gly Gly Arg Glu Asp Glu Gly Pro Pro Gly Tyr Pro Glu Pro
                405                 410                 415 ctg gcg ccg ggg cat ggc tcc cca ttc ccc agc ctg tcc aag aag gat    1296
Leu Ala Pro Gly His Gly Ser Pro Phe Pro Ser Leu Ser Lys Lys Asp
            420                 425                 430 ctg gac ctc atg ctc ctg gac gac tca ctg cta ccg ctg gcc tct gat    1344
Leu Asp Leu Met Leu Leu Asp Asp Ser Leu Leu Pro Leu Ala Ser Asp
        435                 440                 445 cca ctt ctg tcc acc atg tcc ccc gag gcc tcc aag gcc agc agc cgc    1392
Pro Leu Leu Ser Thr Met Ser Pro Glu Ala Ser Lys Ala Ser Ser Arg
    450                 455                 460 cgg agc agc ttc agc atg gag gag ggc gat gtg ctg tga                1431
Arg Ser Ser Phe Ser Met Glu Glu Gly Asp Val Leu
465                 470                 475
```

<210> SEQ ID NO 2
<211> LENGTH: 476
<212> TYPE: PRT
<213> ORGANISM: Homo sapiens

<400> SEQUENCE: 2

```
Met Ala Ser Arg Ile Gly Leu Arg Met Gln Leu Met Arg Glu Gln Ala
1               5                   10                  15

Gln Gln Glu Glu Gln Arg Glu Arg Met Gln Gln Ala Val Met His
            20                  25                  30

Tyr Met Gln Gln Gln Gln Gln Gln Gln Gln Leu Gly Gly Pro
        35                  40                  45

Pro Thr Pro Ala Ile Asn Thr Pro Val His Phe Gln Ser Pro Pro
    50                  55                  60

Val Pro Gly Glu Val Leu Lys Val Gln Ser Tyr Leu Glu Asn Pro Thr
65                  70                  75                  80

Ser Tyr His Leu Gln Gln Ser Gln His Gln Lys Val Arg Glu Tyr Leu
                85                  90                  95

Ser Glu Thr Tyr Gly Asn Lys Phe Ala Ala His Ile Ser Pro Ala Gln
            100                 105                 110

Gly Ser Pro Lys Pro Pro Pro Ala Ala Ser Pro Gly Val Arg Ala Gly
        115                 120                 125

His Val Leu Ser Ser Ser Ala Gly Asn Ser Ala Pro Asn Ser Pro Met
    130                 135                 140

Ala Met Leu His Ile Gly Ser Asn Pro Glu Arg Glu Leu Asp Asp Val
145                 150                 155                 160
```

```
Ile Asp Asn Ile Met Arg Leu Asp Asp Val Leu Gly Tyr Ile Asn Pro
            165                 170                 175

Glu Met Gln Met Pro Asn Thr Leu Pro Leu Ser Ser Ser His Leu Asn
            180                 185                 190

Val Tyr Ser Ser Asp Pro Gln Val Thr Ala Ser Leu Val Gly Val Thr
        195                 200                 205

Ser Ser Ser Cys Pro Ala Asp Leu Thr Gln Lys Arg Glu Leu Thr Asp
    210                 215                 220

Ala Glu Ser Arg Ala Leu Ala Lys Glu Arg Gln Lys Lys Asp Asn His
225                 230                 235                 240

Asn Leu Ile Glu Arg Arg Arg Phe Asn Ile Asn Asp Arg Ile Lys
            245                 250                 255

Glu Leu Gly Met Leu Ile Pro Lys Ala Asn Asp Leu Asp Val Arg Trp
            260                 265                 270

Asn Lys Gly Thr Ile Leu Lys Ala Ser Val Asp Tyr Ile Arg Arg Met
        275                 280                 285

Gln Lys Asp Leu Gln Lys Ser Arg Glu Leu Glu Asn His Ser Arg Arg
    290                 295                 300

Leu Glu Met Thr Asn Lys Gln Leu Trp Leu Arg Ile Gln Glu Leu Glu
305                 310                 315                 320

Met Gln Ala Arg Val His Gly Leu Pro Thr Thr Ser Pro Ser Gly Met
            325                 330                 335

Asn Met Ala Glu Leu Ala Gln Gln Val Val Lys Gln Glu Leu Pro Ser
            340                 345                 350

Glu Glu Gly Pro Gly Glu Ala Leu Met Leu Gly Ala Gly Val Pro Asp
        355                 360                 365

Pro Glu Pro Leu Pro Ala Leu Pro Pro Gln Ala Pro Leu Pro Leu Pro
    370                 375                 380

Thr Gln Pro Pro Ser Pro Phe His His Leu Asp Phe Ser His Ser Leu
385                 390                 395                 400

Ser Phe Gly Gly Arg Glu Asp Glu Gly Pro Pro Gly Tyr Pro Glu Pro
            405                 410                 415

Leu Ala Pro Gly His Gly Ser Pro Phe Pro Ser Leu Ser Lys Lys Asp
            420                 425                 430

Leu Asp Leu Met Leu Leu Asp Asp Ser Leu Leu Pro Leu Ala Ser Asp
        435                 440                 445

Pro Leu Leu Ser Thr Met Ser Pro Glu Ala Ser Lys Ala Ser Ser Arg
    450                 455                 460

Arg Ser Ser Phe Ser Met Glu Glu Gly Asp Val Leu
465                 470                 475

<210> SEQ ID NO 3
<211> LENGTH: 150
<212> TYPE: DNA
<213> ORGANISM: Artificial Sequence
<220> FEATURE:
<223> OTHER INFORMATION: DNA encoding for a variant fragment of TFEB
<220> FEATURE:
<221> NAME/KEY: CDS
<222> LOCATION: (1)..(150)

<400> SEQUENCE: 3 ccc cca cca gcc gcc tcc cca ggg gtg cga gct gga cac gtg ctg tcc        48
Pro Pro Pro Ala Ala Ser Pro Gly Val Arg Ala Gly His Val Leu Ser
1               5                   10                  15 tcc tcc gct ggc aac agt gct ccc aat gcc ccc atg gcc atg ctg cac        96
Ser Ser Ala Gly Asn Ser Ala Pro Asn Ala Pro Met Ala Met Leu His
```

```
                        20                  25                  30
att ggc tcc aac cct gag agg gag ttg gat gat gtc att gac aac att    144
Ile Gly Ser Asn Pro Glu Arg Glu Leu Asp Asp Val Ile Asp Asn Ile
        35                  40                  45 atg cgt                                                            150
Met Arg
    50

<210> SEQ ID NO 4
<211> LENGTH: 50
<212> TYPE: PRT
<213> ORGANISM: Artificial Sequence
<220> FEATURE:
<223> OTHER INFORMATION: Synthetic Construct

<400> SEQUENCE: 4

Pro Pro Pro Ala Ala Ser Pro Gly Val Arg Ala Gly His Val Leu Ser
1               5                   10                  15

Ser Ser Ala Gly Asn Ser Ala Pro Asn Ala Pro Met Ala Met Leu His
            20                  25                  30

Ile Gly Ser Asn Pro Glu Arg Glu Leu Asp Asp Val Ile Asp Asn Ile
        35                  40                  45

Met Arg
    50
```